United States Patent
Askew et al.

(10) Patent No.: US 9,624,169 B2
(45) Date of Patent: Apr. 18, 2017

(54) ARYL- AND HETEROARYL-PYRROLIDINE-2-CARBOXAMIDE COMPOUNDS

(71) Applicant: SciFluor Life Sciences, Inc., Cambridge, MA (US)

(72) Inventors: Ben C. Askew, Marshfield, MA (US); Takeru Furuya, Cambridge, MA (US)

(73) Assignee: SciFluor Life Sciences, Inc., Cambridge, MA (US)

( * ) Notice: Subject to any disclaimer, the term of this patent is extended or adjusted under 35 U.S.C. 154(b) by 0 days.

(21) Appl. No.: 15/081,222

(22) Filed: Mar. 25, 2016

(65) Prior Publication Data

US 2016/0280644 A1    Sep. 29, 2016

Related U.S. Application Data

(60) Provisional application No. 62/139,065, filed on Mar. 27, 2015.

(51) Int. Cl.
| | | |
|---|---|---|
| *C07D 207/16* | (2006.01) | |
| *C07D 401/04* | (2006.01) | |
| *C07D 403/04* | (2006.01) | |
| *C07D 487/10* | (2006.01) | |

(52) U.S. Cl.
CPC ......... *C07D 207/16* (2013.01); *C07D 401/04* (2013.01); *C07D 403/04* (2013.01); *C07D 487/10* (2013.01)

(58) Field of Classification Search
None
See application file for complete search history.

(56) References Cited

FOREIGN PATENT DOCUMENTS

| IT | WO 2007042250 A1 * | 4/2007 | ........... C07D 207/22 |
|---|---|---|---|
| WO | WO 2007/042240 A1 | 4/2007 | |
| WO | WO 2007/042250 A1 | 4/2007 | |
| WO | WO 2008/090114 A1 | 7/2008 | |
| WO | WO 2008/122546 A1 | 10/2008 | |

OTHER PUBLICATIONS

Byrn, Stephen. Solid-State Chemistry of Drugs, 2nd Ed. (1999), Ch. 11 Hydrates and Solvates, 233-247, 233.*
Morissette, Sherry. Adv. Drug Delivery Rev. 2004, 56, 275-300.*
Rouhi, A. Maureen. Chem. & Eng. News, (2003), 81(8), 32-35.*
Mantegazza, Massimo. Lancet Neurol (2010) 9: 413-424.*
Bialer, Meir. Nature Reviews: Drug discovery. 9 (2010) 68-82.*
SAMHSA. Substance Abuse and Mental Health Services Administration. Substance use disorder. (2015) Web <http://www.samhsa.gov/disorders/substance-use>.*
Mayo Clinic. Mood Disorders. (2016). Web < http://www.mayoclinic.org/diseases-conditions/mood-disorders/basics/definition/con-20035907>.*
McElroy, Susan. Therapeutics and Clinical Risk Management 2012:8 219-241.*
Large et al., "The efficacy of sodium channel blockers to prevent phencyclidine-induced cognitive dysfunction in the rat: potential for novel treatments for schizophrenia", *Journal of Pharmacology and Experimental Therapeutics*, 2011, vol. 338, No. 1, pp. 100-113.

* cited by examiner

*Primary Examiner* — Golam M M Shameem
*Assistant Examiner* — Laura Daniel
(74) *Attorney, Agent, or Firm* — Cooley LLP; Ivor R. Elrifi; Heidi A. Erlacher

(57) ABSTRACT

The application relates to novel compounds and their use in treating and preventing diseases and conditions mediated by modulation of voltage-gated sodium channels. Novel aryl- and heteroaryl-pyrrolidine-2-carboxamide compounds and pharmaceutically acceptable salts or solvates thereof and their use are described.

19 Claims, 4 Drawing Sheets

ARYL- AND HETEROARYL-PYRROLIDINE-2-CARBOXAMIDE COMPOUNDS

RELATED APPLICATION

This application claims priority to, and the benefit of, U.S. Provisional Application No. 62/139,065, filed on Mar. 27, 2015, the contents of which are incorporated by reference in their entirety.

BACKGROUND

Voltage-gated sodium channels are central to the generation of action potentials in all excitable cells such as neurons and myocytes. They play key roles in excitable tissue including brain, smooth muscles of the gastrointestinal tract, skeletal muscles, the peripheral nervous system, spinal cord and airway. As such they play key roles in a variety of disease states such as epilepsy, pain, ataxia, multiple sclerosis, irritable bowel disease, urinary incontinence and visceral pain, as well as an array of psychiatry dysfunctions such as anxiety and depression. The efficacy of sodium channel blockers currently utilized for the treatment of the disease states such as those described above have been to a large extent limited by a number of side effects. These side effects include various CNS disturbances such as blurred vision, dizziness, nausea, and sedation as well as more potentially life threatening cardiac arrhythmias and cardiac failure. Furthermore, the voltage-gated sodium channel family consists of 10 subtypes and many of the current sodium channel blockers do not distinguish among these subtypes. Accordingly, there remains a need to develop additional sodium channel inhibitors, preferably those with higher potency and fewer side effects. There is also a need to develop subtype selective sodium channel inhibitors.

SUMMARY OF THE DISCLOSURE

The present application relates to novel modulators of voltage-gated sodium channels and their use. The present application relates to the synthesis of modulators of voltage-gated sodium channels.

The application provides a compound of formula I:

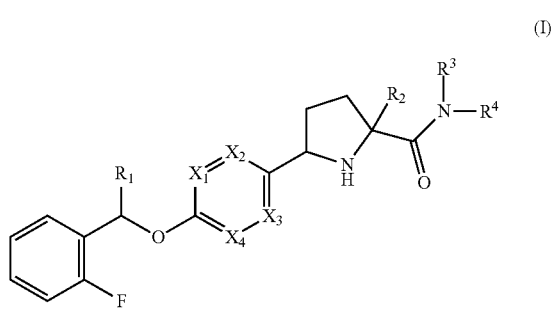

(I)

or a pharmaceutically acceptable salt or solvate thereof, wherein each of the variables in formula I is defined herein.

The application also provides methods of synthesizing the compound of the present application.

The application also provides methods of treating or preventing a disease or condition related to the modulation of voltage-gated sodium channels, such as those described herein, comprising administering a compound of the present application to a subject in need thereof.

The application also provides use of a compound of the present application for treating or preventing a disease or condition related to the modulation of voltage-gated sodium channels, such as those described herein, or use of a compound of the present application in the manufacture of a medicament for treating or preventing a disease or condition related to the modulation of voltage-gated sodium channels, such as those described herein.

DETAILED DESCRIPTION OF THE DISCLOSURE

Figure 1A:
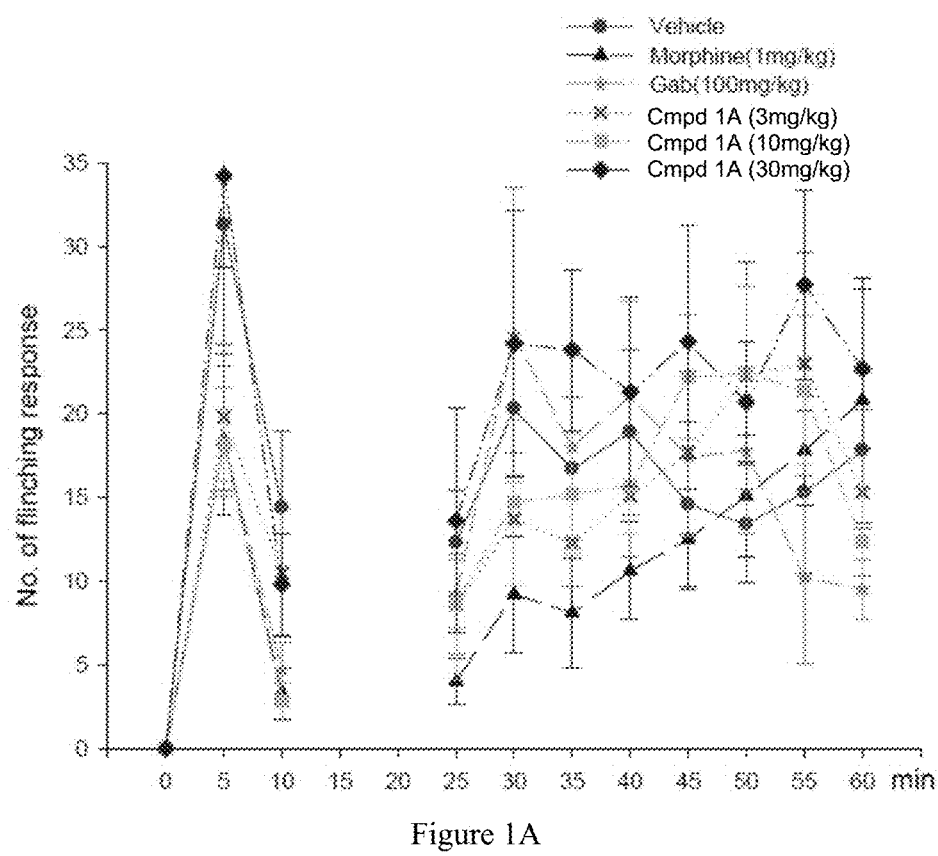
FIG. 1A shows the number of flinching response as a result of formalin induced pain in rats treated with Compound 1A or indicated reagents during the 60 minutes after formalin injection.

For purposes of the present application, the following definitions will be used (unless expressly stated otherwise).

The term "a compound of the application" or "compounds of the application" refers to a compound(s) disclosed herein, e.g., a compound(s) of the application includes a compound(s) of any of the formulae described herein, including formulae I, II, III, IV, V, VI, VII, VIII, or IX and/or a compound(s) explicitly disclosed herein. Whenever the term is used in the context of the present application it is to be understood that the reference is being made to the free base or deuterium labeled compounds, or the corresponding pharmaceutically acceptable salts or solvates thereof, provided that such is possible and/or appropriate under the circumstances.

The term "pharmaceutical" or "pharmaceutically acceptable" when used herein as an adjective, means substantially non-toxic and substantially non-deleterious to the recipient.

By "pharmaceutical formulation" it is further meant that the carrier, solvent, excipient(s) and salt must be compatible with the active ingredient of the formulation (e.g., a compound of the application). It is understood by those of ordinary skill in this art that the terms "pharmaceutical formulation" and "pharmaceutical composition" are generally interchangeable, and they are so used for the purposes of this application.

Some of the compounds of the present application may exist in unsolvated as well as solvated forms such as, for example, hydrates.

"Solvate" means a solvent addition form that contains either a stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; when the solvent is alcohol, the solvate formed is an alcoholate. Hydrates are formed by the combination of one or more molecules of water with one of the substances in which the water retains its molecular state as $H_2O$, such combination being able to form one or more hydrate. In the hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates are sesquihydrates, monohydrates, dihydrates or trihydrates. Equally suitable are the hydrates of salts of the compounds of the application.

The present application also includes metabolites of the compounds described herein.

Physiologically acceptable, i.e., pharmaceutically compatible, salts can be salts of the compounds of the application with inorganic or organic acids. Preference is given to salts with inorganic acids, such as, for example, hydrochloric acid, hydrobromic acid, phosphoric acid or sulphuric acid, or to salts with organic carboxylic or sulphonic acids, such as, for example, acetic acid, trifluoroacetic acid, propionic acid, maleic acid, fumaric acid, malic acid, citric acid, tartaric acid, lactic acid, benzoic acid, or methanesulphonic acid, ethanesulphonic acid, benzenesulphonic acid, toluenesulphonic acid or naphthalenedisulphonic acid.

Other pharmaceutically compatible salts which may be mentioned are salts with customary bases, such as, for example, alkali metal salts (for example sodium or potassium salts), alkaline earth metal salts (for example calcium or magnesium salts) or ammonium salts, derived from ammonia or organic amines, such as, for example, diethylamine, triethylamine, ethyldiisopropylamine, procaine, dibenzylamine, N-methylmorpholine, dihydroabietylamine or methylpiperidine.

When any variable (e.g., X) occurs more than one time in any constituent or formula for a compound, its definition at each occurrence is independent of its definition at every other occurrence. Thus, for example, if a group is shown to be substituted with one or more X moieties, then X at each occurrence is selected independently from the moieties or groups defined for X. Also, combinations of substituents and/or variables are permissible, but only if such combinations result in stable compounds within a designated atom's normal valency.

In the present specification, the structural formula of the compound represents a certain isomer for convenience in some cases, but the present application includes all isomers, such as geometrical isomers, optical isomers based on an asymmetrical carbon, and stereoisomers.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

As used herein, the term "treat," "treating," or "treatment" is meant decreasing the symptoms, markers, and/or any negative effects of a condition in any appreciable degree in a patient who currently has the condition. In some embodiments, treatment may be administered to a subject who exhibits only early signs of the condition for the purpose of decreasing the risk of developing the disease, disorder, and/or condition.

As used herein, the term "prevent," "prevention," or "preventing" refers to any method to partially or completely prevent or delay the onset of one or more symptoms or features of a disease, disorder, and/or condition. Prevention may be administered to a subject who does not exhibit signs of a disease, disorder, and/or condition.

As used herein, "subject" means a human or animal (in the case of an animal, more typically a mammal). In one aspect, the subject is a human. In one aspect, the subject is a male. In one aspect, the subject is a female.

The problem to be solved by the present application is the identification of compounds which modulate voltage-gated sodium channels. The compounds of the application are for use the treatment and/or prevention of diseases and conditions mediated by modulation of voltage-gated sodium channels. The voltage-gated sodium channel family consists of 10 subtypes, four of which are brain specific, NaV1.1, 1.2, 1.3 and 1.6. Of the other subtypes, NaV1.4 is found only in skeletal muscle, NaV1.5 is specific to cardiac muscle, and NaV1.7, 1.8, and 1.9 are found predominantly in sensory neurons. The hypothesized binding site for use-dependent sodium channel blockers is highly conserved between all the subtypes. As a result, drugs such as lidocaine, lamotrigine and carbamazepine that block voltage-gated sodium channels do not distinguish between the subtypes. However, selectivity can be achieved as a result of the different frequencies at which the channels normally operate.

Although drugs for treating or preventing diseases or conditions mediated by modulation of voltage-gated sodium channels are available, these drugs are often not suitable for many patients for a variety of reasons. For example, some drugs do not distinguish among subtypes and/or have adverse side effects, such as CNS disturbances, including blurred vision, dizziness, nausea, and sedation, as well as more potentially life threatening cardiac arrhythmias and cardiac failure. In some instances, the drugs do not have a profile that is suitable for oral administration, for example in terms of exposure (Cmax) and/or bioavailability. The present application provides the solution of new modulators of voltage-gated sodium channels for the treatment and/or prevention of the diseases or conditions described herein such as pain, depression and mood disorders, and epilepsy. The compounds described herein have the advantage of providing improved potency, selectivity, tissue penetration, half-life, and/or metabolic stability.

Compounds of the Application

The present application relates to novel modulators of voltage-gated sodium channels and their use. The present application relates to the synthesis of modulators of voltage-gated sodium channels.

The application provides a compound of formula I:

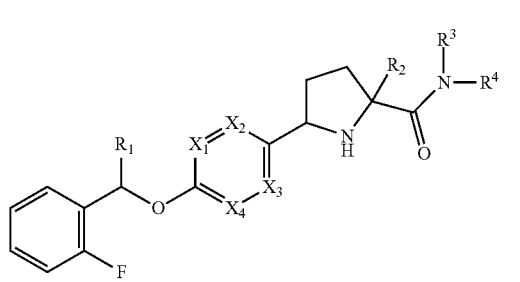

or a pharmaceutically acceptable salt or solvate thereof, wherein
$X_1$, $X_2$, $X_3$, and $X_4$ are each independently selected from N and CH;
$R_1$ is selected from hydrogen, F, $CF_3$, $CH_2F$, $CHF_2$, $OCF_3$, $OCH_2F$, and $OCHF_2$;
$R_2$ is hydrogen; and
$R_3$ and $R_4$ are each independently selected from hydrogen and $C_1$-$C_3$ alkyl;
or $R_2$ and $R_3$ or $R_4$ taken together with the atoms to which they are attached form a 5-membered ring,
provided that when $R_1$, $R_2$, $R_3$ and $R_4$ are each hydrogen, then one or more of $X_1$, $X_2$, $X_3$, and $X_4$ are N, and
provided that when $R_1$ is hydrogen, $X_1$, $X_2$, $X_3$, and $X_4$ are each CH, and $R_2$ and $R_3$ or $R_4$ taken together with the atoms to which they are attached form a 5-membered ring, then the remaining $R_3$ or $R_4$ is not methyl or hydrogen.

While all of the compounds of this application are useful, certain classes are preferred. The following paragraphs describe certain preferred classes of compounds of formula I, wherein:
a-1) $R_2$ and $R_3$ or $R_4$ taken together with the atoms to which they are attached form a 5-membered ring;
a-2) $R_3$ or $R_4$ is hydrogen;
a-3) $R_2$, $R_3$, and $R_4$ are each hydrogen;
a-4) $R_1$ is hydrogen;
a-5) $R_1$ is selected from hydrogen and F;
a-6) $R_1$ is selected from F, $CF_3$, $CH_2F$, $CHF_2$, $OCF_3$, $OCH_2F$, and $OCHF_2$;
a-7) $R_1$ is selected from F, $CF_3$, $CH_2F$, and $CHF_2$;
a-8) $R_1$ is selected from $CF_3$, $CH_2F$, and $CHF_2$;
a-9) $R_1$ is $CF_3$;
a-10) $R_1$ is selected from $OCF_3$, $OCH_2F$, and $OCHF_2$;
a-11) $R_1$ is $OCF_3$;
a-12) $R_1$ is selected from F, $CF_3$, and $OCF_3$;
a-13) $R_1$ is selected from $CF_3$ and $OCF_3$;
a-14) the carbon atom attached to $R_1$ is in the R-configuration;
a-15) the carbon atom attached to $R_1$ is in the S-configuration;
a-16) $R_4$ is $C_1$-$C_3$ alkyl;
a-17) $R_4$ is methyl;
a-18) $R_4$ is ethyl;
a-19) $R_4$ is propyl;
a-20) $R_4$ hydrogen; and
a-21) the carbon atom attached to $R_1$ is a mixture of R- and S-configuration.

It will be understood that the above classes may be combined to form additional classes, as for example the combination of selections for two or more substituents.

For example, for formula I, class a-1) can be combined with one of classes a-4) through a-13);

For formula I, class a-1) can be combined with one of classes a-4) through a-13) and further combined with one of classes a-14), a-15), or a-21);

For formula I, class a-1) can be combined with one of classes a-4) through a-13) and further combined with one of classes a-14), a-15), or a-21) and further combined with one of classes a-16) through a-20);

For formula I, one of classes a-4) through a-13) can be combined with one of classes a-14), a-15) or a-21);

For formula I, one of classes a-4) through a-13) can be combined with one of classes a-14), a-15) or a-21) and further combined with one of classes a-16) through a-20).

The application provides a compound of formula II:

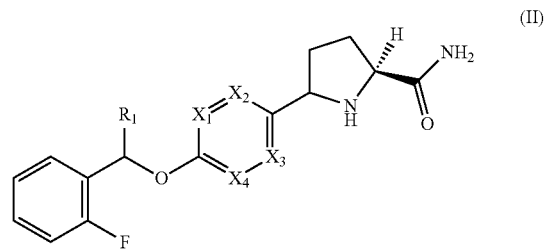

or a pharmaceutically acceptable salt or solvate thereof, wherein
$X_1$, $X_2$, $X_3$, and $X_4$ are each independently selected from N and CH; and $R_1$ is selected from hydrogen, F, $CF_3$, $CH_2F$, $CHF_2$, $OCF_3$, $OCH_2F$, and $OCHF_2$, provided that when $R_1$ is hydrogen, then one or more of $X_1$, $X_2$, $X_3$, and $X_4$ are N.

While all of the compounds of this application are useful, certain classes are preferred. The following paragraphs describe certain preferred classes of compounds of formula II, wherein:

b-1) $R_1$ is hydrogen;
b-2) $R_1$ is selected from hydrogen and F;
b-3) $R_1$ is selected from F, $CF_3$, $CH_2F$, $CHF_2$, $OCF_3$, $OCH_2F$, and $OCHF_2$;
b-4) $R_1$ is selected from F, $CF_3$, $CH_2F$, and $CHF_2$;
b-5) $R_1$ is selected from $CF_3$, $CH_2F$, and $CHF_2$;
b-6) $R_1$ is $CF_3$;
b-7) $R_1$ is selected from $OCF_3$, $OCH_2F$, and $OCHF_2$;
b-8) $R_1$ is $OCF_3$;
b-9) $R_1$ is selected from F, $CF_3$, and $OCF_3$;
b-10) $R_1$ is selected from $CF_3$ and $OCF_3$;
b-11) the carbon atom attached to $R_1$ is in the R-configuration;
b-12) the carbon atom attached to $R_1$ is in the S-configuration; and
b-13) the carbon atom attached to $R_1$ is a mixture of R- and S-configuration.

It will be understood that one of classes b-1) through b-10) can be combined with one of classes b-11) through b-13).

The application provides a compound of formula III:

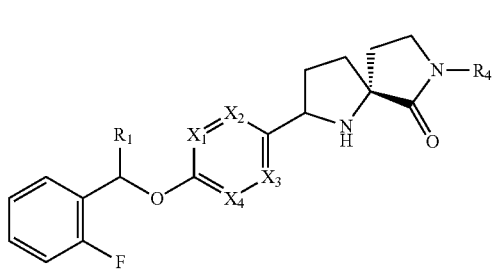

(III)

or a pharmaceutically acceptable salt or solvate thereof, wherein
$X_1$, $X_2$, $X_3$, and $X_4$ are each independently selected from N and CH;
$R_1$ is selected from hydrogen, F, $CF_3$, $CH_2F$, $CHF_2$, $OCF_3$, $OCH_2F$, and $OCHF_2$; and
$R_4$ is selected from hydrogen and $C_1$-$C_3$ alkyl, provided that when $R_1$ is hydrogen and $X_1$, $X_2$, $X_3$, and $X_4$ are each CH, then $R_4$ is not methyl or hydrogen.

While all of the compounds of this application are useful, certain classes are preferred. The following paragraphs describe certain preferred classes of compounds of formula III, wherein:

c-1) $R_1$ is hydrogen;
c-2) $R_1$ is selected from hydrogen and F;
c-3) $R_1$ is selected from F, $CF_3$, $CH_2F$, $CHF_2$, $OCF_3$, $OCH_2F$, and $OCHF_2$;
c-4) $R_1$ is selected from F, $CF_3$, $CH_2F$, and $CHF_2$;
c-5) $R_1$ is selected from $CF_3$, $CH_2F$, and $CHF_2$;
c-6) $R_1$ is $CF_3$;
c-7) $R_1$ is selected from $OCF_3$, $OCH_2F$, and $OCHF_2$;
c-8) $R_1$ is $OCF_3$;
c-9) $R_1$ is selected from F, $CF_3$, and $OCF_3$;
c-10) $R_1$ is selected from $CF_3$ and $OCF_3$;
c-11) the carbon atom attached to $R_1$ is in the R-configuration;
c-12) the carbon atom attached to $R_1$ is in the S-configuration;
c-13) $R_4$ is $C_1$-$C_3$ alkyl;
c-14) $R_4$ is methyl;
c-15) $R_4$ is ethyl;
c-16) $R_4$ is propyl;
c-17) $R_4$ hydrogen; and
c-18) the carbon atom attached to $R_1$ is a mixture of R- and S-configuration.

It will be understood that the above classes may be combined to form additional classes, as for example the combination of selections for two or more substituents.

For example, for formula III, one of classes c-1) through c-10) can be combined with one of classes c-11), c-12), or c-18);

For formula III, one of classes c-1) through c-10) can be combined with one of classes c-11), c-12), or c-18) and further combined with one of classes c-13) through c-17).

The application provides a compound of formula IV:

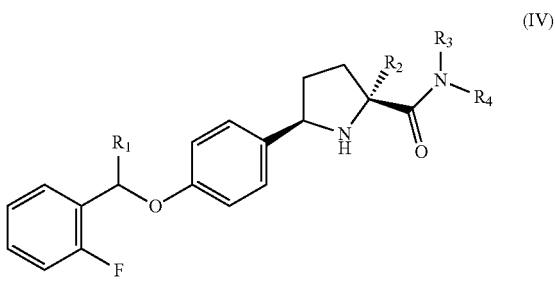

(IV)

or a pharmaceutically acceptable salt or solvate thereof, wherein
$R_1$ is selected from hydrogen, F, $CF_3$, $CH_2F$, $CHF_2$, $OCF_3$, $OCH_2F$, and $OCHF_2$;
$R_2$ is hydrogen; and
$R_3$ and $R_4$ are each independently selected from hydrogen and $C_1$-$C_3$ alkyl;
or $R_2$ and $R_3$ or $R_4$ taken together with the atoms to which they are attached form a 5-membered ring, provided that when $R_2$, $R_3$ and $R_4$ are each hydrogen then $R_1$ is not hydrogen and provided that when $R_1$ is hydrogen, and $R_2$ and $R_3$ or $R_4$ taken together with the atoms to which they are attached form a 5-membered ring, then the remaining $R_3$ or $R_4$ is not methyl or hydrogen.

While all of the compounds of this application are useful, certain classes are preferred. The following paragraphs describe certain preferred classes of compounds of formula IV, wherein:

d-1) $R_2$ and $R_3$ or $R_4$ taken together with the atoms to which they are attached form a 5-membered ring;
d-2) $R_3$ or $R_4$ is hydrogen;
d-3) $R_2$, $R_3$, and $R_4$ are each hydrogen;
d-4) $R_1$ is hydrogen;
d-5) $R_1$ is selected from hydrogen and F;
d-6) $R_1$ is selected from F, $CF_3$, $CH_2F$, $CHF_2$, $OCF_3$, $OCH_2F$, and $OCHF_2$;
d-7) $R_1$ is selected from F, $CF_3$, $CH_2F$, and $CHF_2$;
d-8) $R_1$ is selected from $CF_3$, $CH_2F$, and $CHF_2$;
d-9) $R_1$ is $CF_3$;
d-10) $R_1$ is selected from $OCF_3$, $OCH_2F$, and $OCHF_2$;
d-11) $R_1$ is $OCF_3$;
d-12) $R_1$ is selected from F, $CF_3$, and $OCF_3$;

d-13) $R_1$ is selected from $CF_3$ and $OCF_3$;
d-14) the carbon atom attached to $R_1$ is in the R-configuration;
d-15) the carbon atom attached to $R_1$ is in the S-configuration;
d-16) $R_4$ is $C_1$-$C_3$ alkyl;
d-17) $R_4$ is methyl;
d-18) $R_4$ is ethyl;
d-19) $R_4$ is propyl;
d-20) $R_4$ hydrogen;
d-21) the carbon atom attached to $R_1$ is a mixture of R- and S-configuration.

It will be understood that the above classes may be combined to form additional classes, as for example the combination of selections for two or more substituents.

For example, for formula IV, class d-1) can be combined with one of classes d-4) through d-13);

For formula IV, class d-1) can be combined with one of classes d-4) through d-13) and further combined with one of classes d-14), d-15), or d-21);

For formula IV, class d-1) can be combined with one of classes d-4) through d-13) and further combined with one of classes d-14), d-15), or d-21) and further combined with one of classes d-16) through d-20);

For formula IV, one of classes d-4) through d-13) can be combined with one of classes d-14), d-15), or d-21);

For formula IV, one of classes d-4) through d-13) can be combined with one of classes d-14), d-15), or d-21) and further combined with one of classes d-16) through d-20).

The application provides a compound of formula V:

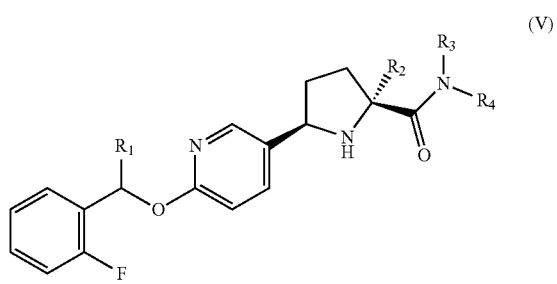

(V)

or a pharmaceutically acceptable salt or solvate thereof, wherein
$R_1$ is selected from hydrogen, F, $CF_3$, $CH_2F$, $CHF_2$, $OCF_3$, $OCH_2F$, and $OCHF_2$;
$R_2$ is hydrogen; and
$R_3$ and $R_4$ are each independently selected from hydrogen and $C_1$-$C_3$ alkyl;
or $R_2$ and $R_3$ or $R_4$ taken together with the atoms to which they are attached form a 5-membered ring.

While all of the compounds of this application are useful, certain classes are preferred. The following paragraphs describe certain preferred classes of compounds of formula V, wherein:
e-1) $R_2$ and $R_3$ or $R_4$ taken together with the atoms to which they are attached form a 5-membered ring;
e-2) $R_3$ or $R_4$ is hydrogen;
e-3) $R_2$, $R_3$, and $R_4$ are each hydrogen;
e-4) $R_1$ is hydrogen;
e-5) $R_1$ is selected from hydrogen and F;
e-6) $R_1$ is selected from F, $CF_3$, $CH_2F$, $CHF_2$, $OCF_3$, $OCH_2F$, and $OCHF_2$;
e-7) $R_1$ is selected from F, $CF_3$, $CH_2F$, and $CHF_2$;
e-8) $R_1$ is selected from $CF_3$, $CH_2F$, and $CHF_2$;
e-9) $R_1$ is $CF_3$;
e-10) $R_1$ is selected from $OCF_3$, $OCH_2F$, and $OCHF_2$;
e-11) $R_1$ is $OCF_3$;
e-12) $R_1$ is selected from F, $CF_3$, and $OCF_3$;
e-13) $R_1$ is selected from $CF_3$ and $OCF_3$;
e-14) the carbon atom attached to $R_1$ is in the R-configuration;
e-15) the carbon atom attached to $R_1$ is in the S-configuration;
e-16) $R_4$ is $C_1$-$C_3$ alkyl;
e-17) $R_4$ is methyl;
e-18) $R_4$ is ethyl;
e-19) $R_4$ is propyl;
e-20) $R_4$ hydrogen; and
e-21) the carbon atom attached to $R_1$ is a mixture of R- and S-configuration.

It will be understood that the above classes may be combined to form additional classes, as for example the combination of selections for two or more substituents.

For example, for formula V, class e-1) can be combined with one of classes e-4) through e-13);

For formula V, class e-1) can be combined with one of classes e-4) through e-13) and further combined with one of classes e-14), e-15), or e-21);

For formula V, class e-1) can be combined with one of classes e-4) through e-13) and further combined with one of classes e-14), e-15), or e-21) and further combined with one of classes e-16) through e-20);

For formula V, one of classes e-4) through e-13) can be combined with one of classes e-14), e-15), or e-21);

For formula V, one of classes e-4) through e-13) can be combined with one of classes e-14), e-15), or e-21) and further combined with one of classes e-16) through e-20).

The application provides a compound of formula VI:

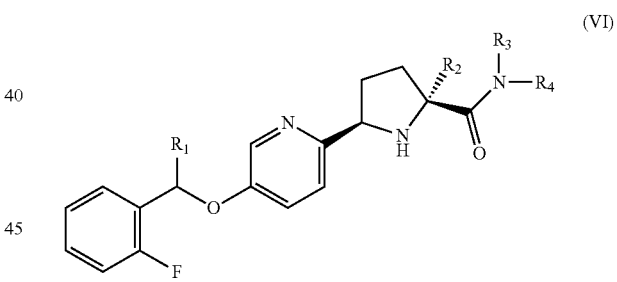

(VI)

or a pharmaceutically acceptable salt or solvate thereof, wherein
$R_1$ is selected from hydrogen, F, $CF_3$, $CH_2F$, $CHF_2$, $OCF_3$, $OCH_2F$, and $OCHF_2$;
$R_2$ is hydrogen; and
$R_3$ and $R_4$ are each independently selected from hydrogen and $C_1$-$C_3$ alkyl;
or $R_2$ and $R_3$ or $R_4$ taken together with the atoms to which they are attached form a 5-membered ring.

While all of the compounds of this application are useful, certain classes are preferred. The following paragraphs describe certain preferred classes of compounds of formula VI, wherein:
f-1) $R_2$ and $R_3$ or $R_4$ taken together with the atoms to which they are attached form a 5-membered ring;
f-2) $R_3$ or $R_4$ is hydrogen;
f-3) $R_2$, $R_3$, and $R_4$ are each hydrogen;
f-4) $R_1$ is hydrogen;
f-5) $R_1$ is selected from hydrogen and F;

f-6) $R_1$ is selected from F, $CF_3$, $CH_2F$, $CHF_2$, $OCF_3$, $OCH_2F$, and $OCHF_2$;
f-7) $R_1$ is selected from F, $CF_3$, $CH_2F$, and $CHF_2$;
f-8) $R_1$ is selected from $CF_3$, $CH_2F$, and $CHF_2$;
f-9) $R_1$ is $CF_3$;
f-10) $R_1$ is selected from $OCF_3$, $OCH_2F$, and $OCHF_2$;
f-11) $R_1$ is $OCF_3$;
f-12) $R_1$ is selected from F, $CF_3$, and $OCF_3$;
f-13) $R_1$ is selected from $CF_3$ and $OCF_3$;
f-14) the carbon atom attached to $R_1$ is in the R-configuration;
f-15) the carbon atom attached to $R_1$ is in the S-configuration;
f-16) $R_4$ is $C_1$-$C_3$ alkyl;
f-17) $R_4$ is methyl;
f-18) $R_4$ is ethyl;
f-19) $R_4$ is propyl;
f-20) $R_4$ hydrogen; and
f-21) the carbon atom attached to $R_1$ is a mixture of R- and S-configuration.

It will be understood that the above classes may be combined to form additional classes, as for example the combination of selections for two or more substituents.

For example, for formula VI, class f-1) can be combined with one of classes f-4) through f-13);

For formula VI, class f-1) can be combined with one of classes f-4) through f-13) and further combined with one of classes f-14), f-15), or f-21);

For formula VI, class f-1) can be combined with one of classes f-4) through f-13) and further combined with one of classes f-14), f-15), or f-21) and further combined with one of classes f-16) through f-20);

For formula VI, one of classes f-4) through f-13) can be combined with one of classes f-14), f-15), or f-21);

For formula VI, one of classes f-4) through f-13) can be combined with one of classes f-14), f-15), or f-21) and further combined with one of classes f-16) through f-20).

The application provides a compound of formula VII:

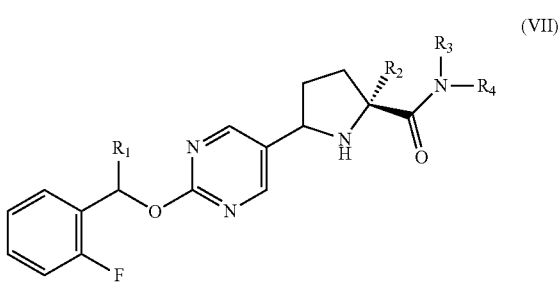

(VII)

or a pharmaceutically acceptable salt or solvate thereof, wherein
$R_1$ is selected from hydrogen, F, $CF_3$, $CH_2F$, $CHF_2$, $OCF_3$, $OCH_2F$, and $OCHF_2$;
$R_2$ is hydrogen; and
$R_3$ and $R_4$ are each independently selected from hydrogen and $C_1$-$C_3$ alkyl;
or $R_2$ and $R_3$ or $R_4$ taken together with the atoms to which they are attached form a 5-membered ring.

While all of the compounds of this application are useful, certain classes are preferred. The following paragraphs describe certain preferred classes of compounds of formula VII, wherein:
g-1) $R_2$ and $R_3$ or $R_4$ taken together with the atoms to which they are attached form a 5-membered ring;
g-2) $R_3$ or $R_4$ is hydrogen;
g-3) $R_2$, $R_3$, and $R_4$ are each hydrogen;
g-4) $R_1$ is hydrogen;
g-5) $R_1$ is selected from hydrogen and F;
g-6) $R_1$ is selected from F, $CF_3$, $CH_2F$, $CHF_2$, $OCF_3$, $OCH_2F$, and $OCHF_2$;
g-7) $R_1$ is selected from F, $CF_3$, $CH_2F$, and $CHF_2$;
g-8) $R_1$ is selected from $CF_3$, $CH_2F$, and $CHF_2$;
g-9) $R_1$ is $CF_3$;
g-10) $R_1$ is selected from $OCF_3$, $OCH_2F$, and $OCHF_2$;
g-11) $R_1$ is $OCF_3$;
g-12) $R_1$ is selected from F, $CF_3$, and $OCF_3$;
g-13) $R_1$ is selected from $CF_3$ and $OCF_3$;
g-14) the carbon atom attached to $R_1$ is in the R-configuration;
g-15) the carbon atom attached to $R_1$ is in the S-configuration;
g-16) $R_4$ is $C_1$-$C_3$ alkyl;
g-17) $R_4$ is methyl;
g-18) $R_4$ is ethyl;
g-19) $R_4$ is propyl;
g-20) $R_4$ hydrogen; and
g-21) the carbon atom attached to $R_1$ is a mixture of R- and S-configuration.

It will be understood that the above classes may be combined to form additional classes, as for example the combination of selections for two or more substituents.

For example, for formula VII, class g-1) can be combined with one of classes g-4) through g-13);

For formula VII, class g-1) can be combined with one of classes g-4) through g-13) and further combined with one of classes g-14), g-15), or g-21);

For formula VII, class g-1) can be combined with one of classes g-4) through g-13) and further combined with one of classes g-14), g-15), or g-21) and further combined with one of classes g-16) through g-20);

For formula VII, one of classes g-4) through g-13) can be combined with one of classes g-14), g-15), or g-21);

For formula VII, one of classes g-4) through g-13) can be combined with one of classes g-14), g-15), or g-21) and further combined with one of classes g-16) through g-20).

The application provides a compound of formula VIII:

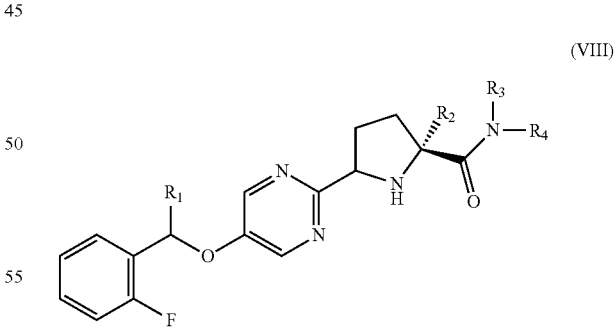

(VIII)

or a pharmaceutically acceptable salt or solvate thereof, wherein
$R_1$ is selected from hydrogen, F, $CF_3$, $CH_2F$, $CHF_2$, $OCF_3$, $OCH_2F$, and $OCHF_2$;
$R_2$ is hydrogen; and
$R_3$ and $R_4$ are each independently selected from hydrogen and $C_1$-$C_3$ alkyl;
or $R_2$ and $R_3$ or $R_4$ taken together with the atoms to which they are attached form a 5-membered ring.

While all of the compounds of this application are useful, certain classes are preferred. The following paragraphs describe certain preferred classes of compounds of formula VIII, wherein:

h-1) $R_2$ and $R_3$ or $R_4$ taken together with the atoms to which they are attached form a 5-membered ring;
h-2) $R_3$ or $R_4$ is hydrogen;
h-3) $R_2$, $R_3$, and $R_4$ are each hydrogen;
h-4) $R_1$ is hydrogen;
h-5) $R_1$ is selected from hydrogen and F;
h-6) $R_1$ is selected from F, $CF_3$, $CH_2F$, $CHF_2$, $OCF_3$, $OCH_2F$, and $OCHF_2$;
h-7) $R_1$ is selected from F, $CF_3$, $CH_2F$, and $CHF_2$;
h-8) $R_1$ is selected from $CF_3$, $CH_2F$, and $CHF_2$;
h-9) $R_1$ is $CF_3$;
h-10) $R_1$ is selected from $OCF_3$, $OCH_2F$, and $OCHF_2$;
h-11) $R_1$ is $OCF_3$;
h-12) $R_1$ is selected from F, $CF_3$, and $OCF_3$;
h-13) $R_1$ is selected from $CF_3$ and $OCF_3$;
h-14) the carbon atom attached to $R_1$ is in the R-configuration;
h-15) the carbon atom attached to $R_1$ is in the S-configuration;
h-16) $R_4$ is $C_1$-$C_3$ alkyl;
h-17) $R_4$ is methyl;
h-18) $R_4$ is ethyl;
h-19) $R_4$ is propyl;
h-20) $R_4$ hydrogen; and
h-21) the carbon atom attached to $R_1$ is a mixture of R- and S-configuration.

It will be understood that the above classes may be combined to form additional classes, as for example the combination of selections for two or more substituents.

For example, for formula VIII, class h-1) can be combined with one of classes h-4) through h-13);

For formula VIII, class h-1) can be combined with one of classes h-4) through h-13) and further combined with one of classes h-14), h-15), or h-21);

For formula VIII, class h-1) can be combined with one of classes h-4) through h-13) and further combined with one of classes h-14), h-15), or h-21) and further combined with one of classes h-16) through h-20);

For formula VIII, one of classes h-4) through h-13) can be combined with one of classes h-14), h-15), or h-21);

For formula VIII, one of classes h-4) through h-13) can be combined with one of classes h-14), h-15), or h-21) and further combined with one of classes h-16) through h-20).

The application provides a compound of formula IX:

(IX)

or a pharmaceutically acceptable salt or solvate thereof, wherein
$R_1$ is selected from hydrogen, F, $CF_3$, $CH_2F$, $CHF_2$, $OCF_3$, $OCH_2F$, and $OCHF_2$;
$R_2$ is hydrogen; and $R_3$ and $R_4$ are each independently selected from hydrogen and $C_1$-$C_3$ alkyl;
or $R_2$ and $R_3$ or $R_4$ taken together with the atoms to which they are attached form a 5-membered ring.

While all of the compounds of this application are useful, certain classes are preferred. The following paragraphs describe certain preferred classes of compounds of formula IX, wherein:

i-1) $R_2$ and $R_3$ or $R_4$ taken together with the atoms to which they are attached form a 5-membered ring;
i-2) $R_3$ or $R_4$ is hydrogen;
i-3) $R_2$, $R_3$, and $R_4$ are each hydrogen;
i-4) $R_1$ is hydrogen;
i-5) $R_1$ is selected from hydrogen and F;
i-6) $R_1$ is selected from F, $CF_3$, $CH_2F$, $CHF_2$, $OCF_3$, $OCH_2F$, and $OCHF_2$;
i-7) $R_1$ is selected from F, $CF_3$, $CH_2F$, and $CHF_2$;
i-8) $R_1$ is selected from $CF_3$, $CH_2F$, and $CHF_2$;
i-9) $R_1$ is $CF_3$;
i-10) $R_1$ is selected from $OCF_3$, $OCH_2F$, and $OCHF_2$;
i-11) $R_1$ is $OCF_3$;
i-12) $R_1$ is selected from F, $CF_3$, and $OCF_3$;
i-13) $R_1$ is selected from $CF_3$ and $OCF_3$;
i-14) the carbon atom attached to $R_1$ is in the R-configuration;
i-15) the carbon atom attached to $R_1$ is in the S-configuration;
i-16) $R_4$ is $C_1$-$C_3$ alkyl;
i-17) $R_4$ is methyl;
i-18) $R_4$ is ethyl;
i-19) $R_4$ is propyl;
i-20) $R_4$ hydrogen; and
i-21) the carbon atom attached to $R_1$ is a mixture of R- and S-configuration.

It will be understood that the above classes may be combined to form additional classes, as for example the combination of selections for two or more substituents.

For example, for formula IX, class i-1) can be combined with one of classes i-4) through i-13);

For formula IX, class i-1) can be combined with one of classes i-4) through i-13) and further combined with one of classes i-14), i-15), or i-21);

For formula IX, class i-1) can be combined with one of classes i-4) through i-13) and further combined with one of classes i-14), i-15), or i-21) and further combined with one of classes i-16) through i-20);

For formula IX, one of classes i-4) through i-13) can be combined with one of classes i-14), i-15), or i-21);

For formula IX, one of classes i-4) through i-13) can be combined with one of classes i-14), i-15), or i-21) and further combined with one of classes i-16) through i-20).

The application provides a compound of Table 1 or a pharmaceutically acceptable salt or solvate thereof.

TABLE 1

| Compound | Chemical Structure |
|---|---|
| 1A | 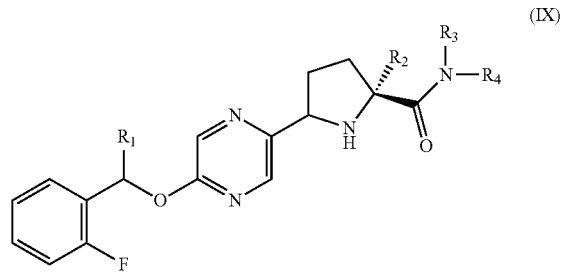 |

TABLE 1-continued

| Compound | Chemical Structure |
|---|---|
| 2A | pyridine with 2-fluorobenzyloxy substituent, linked to pyrrolidine-2-carboxamide |
| 3A | pyridine with 1-(2-fluorophenyl)-2,2,2-trifluoroethoxy substituent, linked to pyrrolidine-2-carboxamide |
| 4A | pyridine (alternative regiochemistry) with 2-fluorobenzyloxy substituent, linked to pyrrolidine-2-carboxamide |
| 5A | pyridine with 1-(2-fluorophenyl)-2,2,2-trifluoroethoxy substituent, linked to pyrrolidine-2-carboxamide |
| 6A | pyrimidine with 2-fluorobenzyloxy substituent, linked to pyrrolidine-2-carboxamide |
| 7A | pyrimidine with 1-(2-fluorophenyl)-2,2,2-trifluoroethoxy substituent, linked to pyrrolidine-2-carboxamide |
| 8A | pyrimidine with 2-fluorobenzyloxy substituent, linked to pyrrolidine-2-carboxamide |
| 9A | pyrimidine with 1-(2-fluorophenyl)-2,2,2-trifluoroethoxy substituent, linked to pyrrolidine-2-carboxamide |
| 10A | pyrazine with 2-fluorobenzyloxy substituent, linked to pyrrolidine-2-carboxamide |
| 11A | pyrazine with 1-(2-fluorophenyl)-2,2,2-trifluoroethoxy substituent, linked to pyrrolidine-2-carboxamide |
| 12A | phenyl with 1-(2-fluorophenyl)-2,2,2-trifluoroethoxy substituent, linked to 1-methyl-2-oxo-1,7-diazaspiro[4.4]nonane |
| 1 | phenyl with 1-(2-fluorophenyl)-2,2,2-trifluoroethoxy substituent, linked to pyrrolidine-2-carboxamide |

TABLE 1-continued

| Compound | Chemical Structure |
|---|---|
| 2 | 5-(2-fluorobenzyloxy)pyridine-prolinamide |
| 3 | 5-(1-(2-fluorophenyl)-2,2,2-trifluoroethoxy)pyridine-prolinamide |
| 4 | 5-(2-fluorobenzyloxy)pyridin-2-yl prolinamide |
| 5 | 5-(1-(2-fluorophenyl)-2,2,2-trifluoroethoxy)pyridin-2-yl prolinamide |
| 6 | 2-(2-fluorobenzyloxy)pyrimidine-prolinamide |
| 7 | 2-(1-(2-fluorophenyl)-2,2,2-trifluoroethoxy)pyrimidine-prolinamide |
| 8 | 5-(2-fluorobenzyloxy)pyrimidin-2-yl prolinamide |
| 9 | 5-(1-(2-fluorophenyl)-2,2,2-trifluoroethoxy)pyrimidin-2-yl prolinamide |
| 10 | 5-(2-fluorobenzyloxy)pyrazine prolinamide |
| 11 | 5-(1-(2-fluorophenyl)-2,2,2-trifluoroethoxy)pyrazine prolinamide |
| 12 | N-methyl spiro pyrrolidinone with 4-(1-(2-fluorophenyl)-2,2,2-trifluoroethoxy)phenyl |

In one aspect, a compound of the application is a pharmaceutically acceptable salt. In one aspect, a compound of the application is a solvate. In one aspect, a compound of the application is a hydrate.

The present application relates to pharmaceutical compositions comprising one of the compounds of the application as an active ingredient. In one aspect, the application provides a pharmaceutical composition comprising at least one compound of formulae I, II, III, IV, V, VI, VII, VIII, or IX, or a pharmaceutically acceptable salt or solvate thereof and one or more pharmaceutically acceptable carrier or excipient. In one aspect, the application provides a pharmaceutical composition comprising at least one compound of Table 1.

The present application relates to a method of synthesizing a compound of the application or a pharmaceutically acceptable salt or solvate thereof. A compound of the application can be synthesized using a variety of methods known in the art. The scheme and description below depicts some general routes for the preparation of a compound of the application.

Scheme 1:

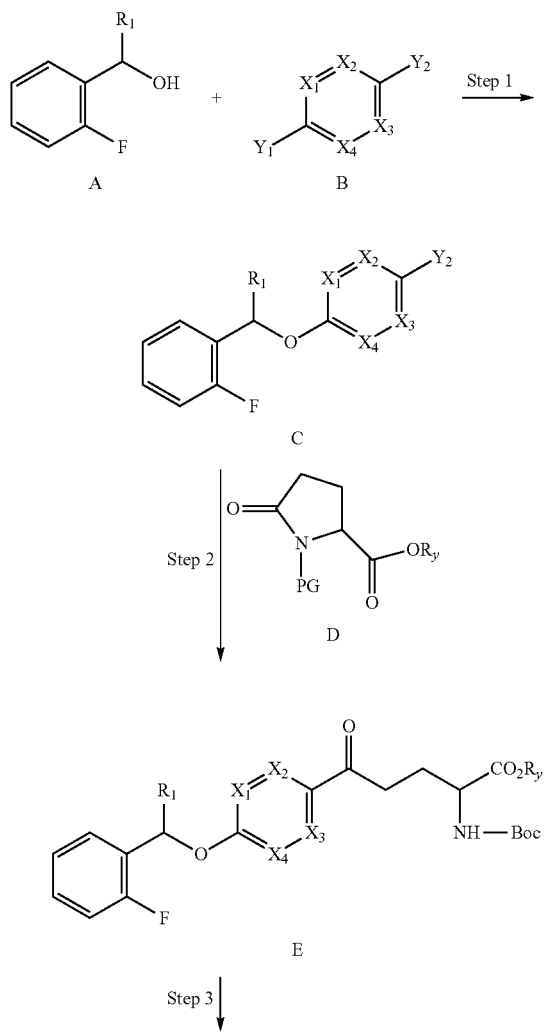

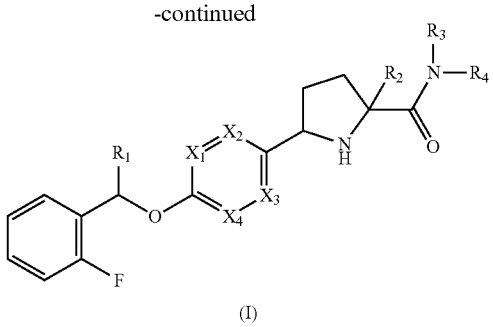

Scheme 1 outlines a preparation for a compound of Formula I. It is understood that Formulae II, III, IV, V, VI, VII, VIII, and IX described herein are subsets of Formula I. Thus, the preparations described for a compound of Formula I can also be applied for the preparation of a compound of Formulae II, III, IV, V, VI, VII, VIII, and IX.

The preparation begins with Compounds A and B, which are commercially available. In Step 1, Compounds A and B are reacted to form Compound C. For example, the hydroxyl group of Compound A can displace $Y_1$ of Compound B (when $Y_1$ is halogen) to form Compound C. Alternatively, the hydroxyl group of Compound A can be converted to a leaving group, e.g., a triflate, which can be displaced by $Y_1$ of Compound B (when $Y_1$ is hydroxyl). Step 2 involves installation of the four carbon chain that cyclized in a later step to form the pyrrolidine ring. For example, Compound C can be treated with an alkyllithium reagent to produce a lithium anion at $Y_2$, which is then reacted with Compound D ($R_y$ is alkyl and PG is protecting group). Step 3 involves cyclization of the four carbon chain to form the pyrrolidine ring followed by conversion of an ester to an amide. For example, Compound D can be treated with acid followed by hydrogenation to form the pyrrolidine ring followed by treatment with ammonia to produce a compound of formula I.

Preparation of compounds having a spirocylic 5-membered ring (e.g., compounds of formula III or compounds of formula I, IV, V, VI, VII, VIII, or IX having $R_2$ and $R_3$ or $R_4$ taken together with the atoms to which they are attached form a 5-membered ring) may involve additional steps as shown below in Scheme 2.

Scheme 2:

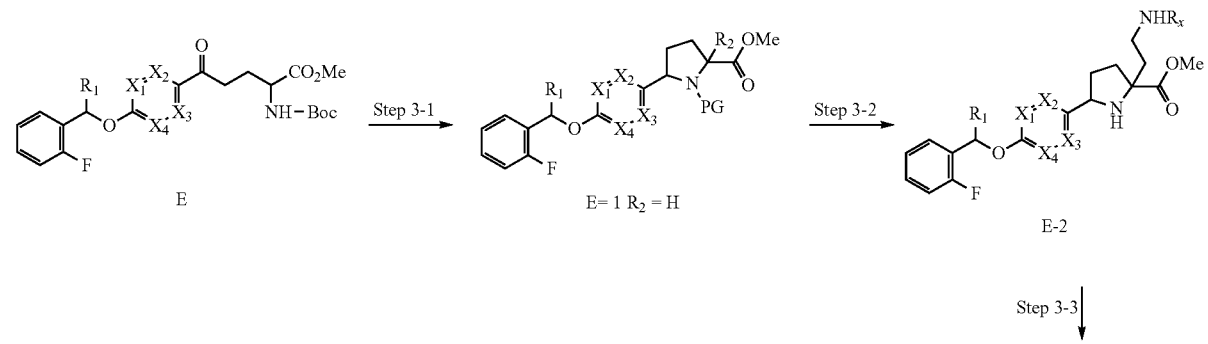

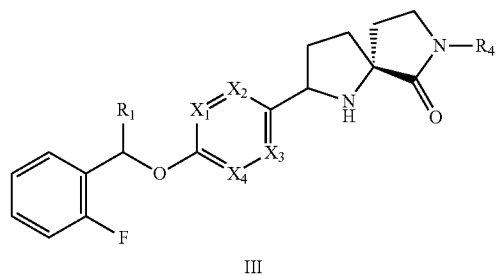

III

Step 3-1 involves cyclization of the four carbon chain to form a pyrrolidine ring (Compound E-1). The cyclization can be carried out using acid followed by hydrogenation. The pyrrolidine ring can be protected with a protecting group (PG), e.g., $CO_2$(t-butyl). Step 3-2 involves attachment of the carbon chain that is cyclized in a later step to form the spirocyclic 5-membered ring. For example, the carbon chain can contain two carbon atoms and a terminal amino group ($R_x$ is an amine protecting group). In another aspect, the carbon chain can be three carbon atoms and have a terminal alkene. The terminal alkene can be oxidized and converted to a terminal amino group. Step 3-3 involves cyclization to form a compound of formula III.

The biological activity of the compounds of the present application can be assessed by various methods known in the art. For example, a formaldehyde solution (e.g., 5%) can be injected subcutaneously to mouse or rat paw to produce a biphasic pain response: an initial pain response shortly after the injection, followed by a second phase of pain response. A compound of the present application may be administered to the mouse or rat, and the initial pain response and/or the second phase pain response can be measured to evaluate the biological activities of the compound.

The present application also comprehends deuterium labeled compounds, which are identical to those recited in formulae I, II, III, IV, V, VI, VII, VIII, or IX, and the compounds listed in Table 1, but for the fact that one or more hydrogen atoms is replaced by a deuterium atom having an abundance of deuterium at that position that is substantially greater than the natural abundance of deuterium, which is 0.015%.

The term "deuterium enrichment factor" as used herein means the ratio between the deuterium abundance and the natural abundance of a deuterium. In one aspect, a compound of the application has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

A compound of the application or a pharmaceutically acceptable salt or solvate thereof that contains the aforementioned deuterium atom(s) is within the scope of the application.

Further, substitution with heavier deuterium, i.e., $^2H$, can afford certain therapeutic advantages resulting from greater metabolic stability, for example increased in vivo half-life or reduced dosage requirements.

In one aspect, a deuterium labeled compound of the application is a pharmaceutically acceptable salt. In one aspect, a deuterium labeled compound of the application is a solvate. In one aspect, a deuterium labeled compound of the application is a hydrate.

The present application relates to pharmaceutical compositions comprising one of the deuterium labeled compounds of the application as an active ingredient. In one aspect, the application provides a pharmaceutical composition comprising at least one deuterium labeled compound of formulae I, II, III, IV, V, VI, VII, VIII, or IX, or a pharmaceutically acceptable salt or solvate thereof and one or more pharmaceutically acceptable carrier or excipient.

The present application relates to a method of synthesizing a deuterium labeled compound of the application or a pharmaceutically acceptable salt or solvate thereof.

The deuterium labeled compounds of the application can be prepared using any of a variety of art-recognized techniques. The deuterium labeled compounds can generally be prepared by carrying out the procedures disclosed in Scheme 1 and the description provided herein for the preparation of a compound of Formula I. For example, a deuterium labeled compound can be prepared by starting with deuterium labeled Compound A and/or substituting a readily available deuterium labeled reagent for a non-deuterium labeled reagent.

Preparation of diastereomers of the compounds of the present application is shown below in Scheme 3.

Scheme 3:

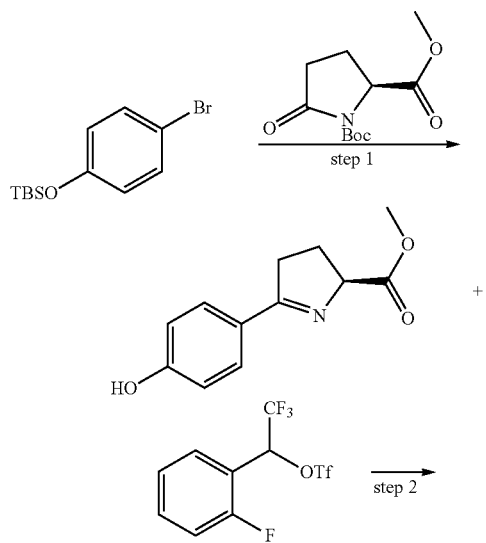

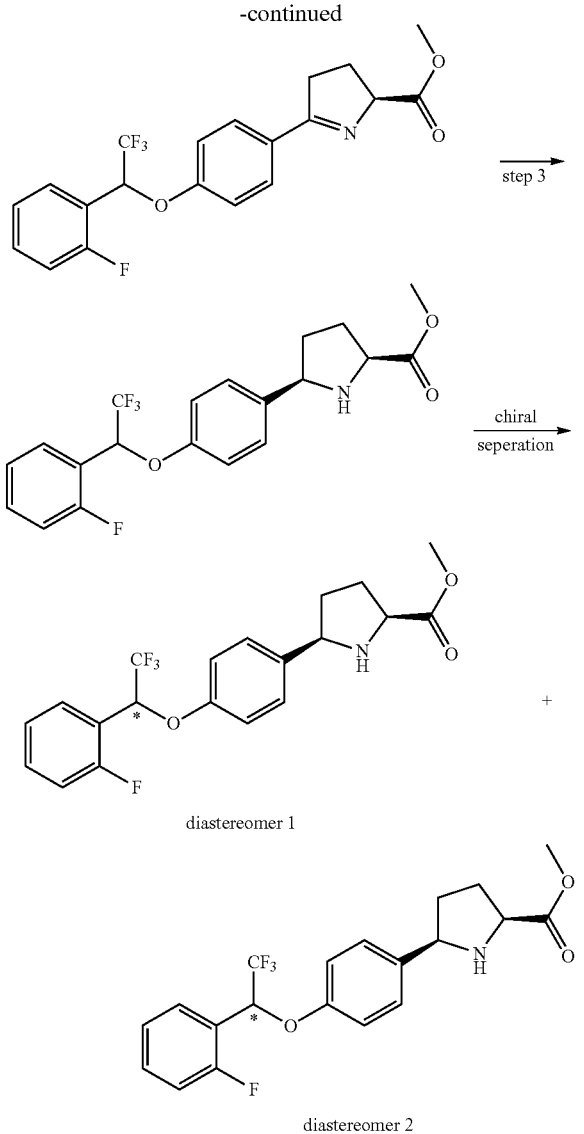

diastereomer 1 diastereomer 2

Scheme 3 illustrates preparation for diastereomers of a compound of the present application. It is understood that diastereomers of other compounds of the present application, such as a compound of Formulae I, II, III, IV, V, VI, VII, VIII, and IX described herein can also be prepared according to Scheme 3.

Methods of Use

The present application relates to methods for the use of compounds of the application. The compounds of the application have a useful pharmacological activity spectrum and are therefore particularly suitable for the prophylaxis and/or treatment of conditions and disorders.

The application provides a method of treating and/or preventing a disease or condition mediated by modulation of voltage-gated sodium channels in a subject comprising administering to the subject in need thereof an effective amount of a compound of the application or a pharmaceutically acceptable salt or solvate thereof.

Voltage-gated sodium channels are responsible for the initial phase of the action potential, which is a wave of electrical depolarization usually initiated at the soma of the neuron and propagated along the nerve axon to the terminals. At the terminals, the action potential triggers the influx of sodium and the release of neurotransmitter. Drugs, such as lidocaine, that block voltage-gated sodium channels are used as local anesthetics. Other sodium channel blockers, such as lamotrigine and carbamazepine are used to treat epilepsy. In the latter case, partial inhibition of voltage-gated sodium channels reduces neuronal excitability and reduces seizure propagation. In the case of local anesthetics, regional block of sodium channels on sensory neurons prevents the conduction of painful stimuli. A key feature of these drugs is their use-dependent mechanism of action. The drugs are thought to stabilize an inactivated configuration of the channel that is adopted rapidly after the channel opens. This inactivated state provides a refractory period before the channel returns to its resting (closed) state ready to be reactivated. As a result, use-dependent sodium channel blockers retard the firing of neurons at high frequency, for example in response to painful stimuli, and will help to prevent repetitive firing during periods of prolonged neuronal depolarization that might occur, for example, during a seizure. Action potentials triggered at low frequencies, for example in the heart, will not be significantly affected by these drugs, although the safety margin differs in each case, since at high enough concentrations each of these drugs is capable of blocking the resting or open states of the channels.

The voltage-gated sodium channel family consists of 10 subtypes, four of which are brain specific, NaV1.1, 1.2, 1.3 and 1.6. Of the other subtypes, NaV1.4 is found only in skeletal muscle, NaV1.5 is specific to cardiac muscle, and NaV1.7, 1.8, and 1.9 are found predominantly in sensory neurons. The hypothesized binding site for use-dependent sodium channel blockers is highly conserved between all the subtypes. As a result, drugs such as lidocaine, lamotrigine and carbamazepine do not distinguish between the subtypes. However, selectivity can be achieved as a result of the different frequencies at which the channels normally operate.

Drugs that block voltage-gated sodium channels in a use-dependent manner are also used in the treatment of bipolar disorder, either to reduce symptoms of mania or depression, or as mood stabilizers to prevent the emergence of mood episodes. Clinical and preclinical evidence also suggests that use-dependent sodium channel blockers may help to reduce the symptoms of schizophrenia. For example, lamotrigine has been shown to reduce symptoms of psychosis induced by ketamine in healthy human volunteers. Furthermore, studies in patients suggest that the drug can augment the antipsychotic efficacy of some atypical antipsychotic drugs, such as clozapine or olanzapine. It is hypothesized that efficacy in these psychiatric disorders may result in part from a reduction of excessive glutamate release. The reduction in glutamate release is thought to be a consequence of use-dependent sodium channel inhibition in key brain areas, such as the frontal cortex. However, interaction with voltage-gated calcium channels may also contribute to the efficacy of these drugs.

The object of the present application is to identify compounds which modulate voltage-gated sodium channels. In one embodiment, a compound of the application is a use dependent sodium channel inhibitors. In another embodiment, a compound of the application is a subtype NaV1.3 sodium channel use dependent inhibitors. In another embodiment, a compound of the application is a use dependent sodium channel inhibitor which has a suitable profile for oral administration, for example in terms of exposure (Cmax) and/or bioavailability. In another embodiment, the application provides a compound which modulates voltage-gated sodium channels and which additionally exhibits monoamine oxidase B inhibition. In a still further embodiment, the application provides a compound which modulates voltage-gated sodium channels and which do not exhibit monoamine oxidase B inhibition.

Without wishing to be bound by theory, diseases or conditions that may be mediated by modulation of voltage-gated sodium channels are selected from the list consisting of [the numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10)]:

i) Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90);

ii) Schizophrenia including the subtypes Paranoid Type (295.30), Disorganized Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9);

iii) Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00);

iv) Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); *Cannabis*-Related Disorders such as *Cannabis* Dependence (304.30), *Cannabis* Abuse (305.20), *Cannabis* Intoxication (292.89), *Cannabis* Intoxication Delirium, *Cannabis*-Induced Psychotic Disorder, *Cannabis*-Induced Anxiety Disorder and *Cannabis*-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide;

v) Enhancement of cognition including the treatment of cognition impairment in other diseases such as schizophrenia, bipolar disorder, depression, other psychiatric disorders and psychotic conditions associated with cognitive impairment, e.g., Alzheimer's disease;

vi) Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome;

vi) Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50);

vii) Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism);

viii) Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23);

ix) Personality Disorders including the subtypes Paranoid Personality Disorder (301.0), Schizoid Personality Disorder (301.20), Schizotypal Personality Disorder (301.22), Antisocial Personality Disorder (301.7), Borderline Personality Disorder (301.83), Histrionic Personality Disorder (301.50), Narcissistic Personality Disorder (301.81), Avoidant Personality Disorder (301.82), Dependent Personality Disorder (301.6), Obsessive-Compulsive Personality Disorder (301.4) and Personality Disorder Not Otherwise Specified (301.9); and x) Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9). xi) Impulse control disorder" including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

In a still further embodiment, diseases or conditions that may be mediated by modulation of voltage gated sodium channels are Nicotine-Related Disorders such as Nicotine Dependence (305.1), Nicotine Withdrawal (292.0) or Nicotine-Related Disorder Not Otherwise Specified (292.9).

The application also provides the use of a compound of the application for the preparation of a medicament for administration to a subject for use in the treatment and/or prevention of conditions and disorders. In one aspect, the medicament is for use in treatment. In one aspect, the medicament is for use in prevention.

The application provides a method of treating pain in a subject comprising administering to the subject an effective amount of a compound of the application or a pharmaceutically acceptable salt or solvate thereof. The compounds of the application are useful for the treatment of chronic, visceral, inflammatory and neuropathic pain syndromes. In one aspect, the application provides a method of treating inflammatory pain or neuropathic pain in a subject comprising administering to the subject an effective amount of a compound of the application or a pharmaceutically acceptable salt or solvate thereof. In one aspect, the pain is inflammatory pain. In one aspect, the pain is neuropathic pain.

Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

In an embodiment, a compound of the application is useful as analgesic. For example a compound of the application may be useful in the treatment of chronic inflammatory pain (e.g., pain associated with rheumatoid arthritis, osteoarthritis, rheumatoid spondylitis, gouty arthritis and juvenile arthritis); musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post-operative pain; headache; toothache; and dysmenorrhea. In one aspect, a compound of the application is useful in the treatment of tinnitus, and as local anaesthetics.

In one embodiment, a compound of the application is useful in the treatment and/or prevention of a disorder treatable and/or preventable with an anti-convulsive agent, such as epilepsy including post-traumatic epilepsy, obsessive compulsive disorders (OCD), sleep disorders (including circadian rhythm disorders, insomnia & narcolepsy), tics (e.g., Giles de la Tourette's syndrome), ataxias, muscular rigidity (spasticity), and temporomandibular joint dysfunction. In one aspect, the application provides a method of treating epilepsy in a subject comprising administering to the subject in need thereof an effective amount of a compound of the application or a pharmaceutically acceptable salt or solvate thereof. In one aspect, a compound of the application has clinical uses for the treatment of epilepsy and partial and generalized tonic seizures.

In embodiment, a compound of the application is useful for the treatment of a neuropsychiatric disorder. The application provides a method of treating a mood disorder in a subject comprising administering to the subject in need thereof an effective amount of a compound of the application or a pharmaceutically acceptable salt or solvate thereof. Mood disorders include depression or depressive disorders. In one aspect, the depressive disorder is for example, a single episodic or recurrent major depressive disorder or dysthymic disorder, or bipolar disorder, for example, bipolar I disorder, bipolar II disorder or cyclothymic disorder; anxiety disorder, such as panic disorder with or without agoraphobia, agoraphobia without history of panic disorder, a specific phobia, for example, specific animal phobia, social phobia, obsessive-compulsive disorder, a stress disorder including post-traumatic stress disorder and acute stress disorder, or generalized anxiety disorder.

The application provides a method of treating compulsive eating disorder or binge eating disorder in a subject comprising administering to the subject in need thereof an effective amount of a compound of the application or a pharmaceutically acceptable salt or solvate thereof.

The application provides a method of treating a substance abuse disorder in a subject comprising administering to the subject in need thereof an effective amount of a compound of the application or a pharmaceutically acceptable salt or solvate thereof.

The application provides a method of treating and/or preventing irritable bowel syndrome and/or related disorders in a subject comprising administering to the subject in need thereof an effective amount of a compound of the application or a pharmaceutically acceptable salt or solvate thereof.

The application provides a method of treating and/or preventing inflammatory bowel disease in a subject comprising administering to the subject in need thereof an effective amount of a compound of the application or a pharmaceutically acceptable salt or solvate thereof. In one aspect, the inflammatory bowel disease is Crohn's disease. In one aspect, the inflammatory bowel disease is ulcerative colitis.

In one embodiment, a compound of the application is useful in neuroprotection and in the treatment of neurodegeneration following stroke, cardiac arrest, pulmonary bypass, traumatic brain injury, spinal cord injury or the like. The application provides a method for neuroprotection under ischaemic conditions caused by stroke or neural trauma in a subject comprising administering to the subject in need thereof an effective amount of a compound of the application or a pharmaceutically acceptable salt or solvate thereof.

The application provides a method of treating and/or preventing multiple sclerosis in a subject comprising administering to the subject in need thereof an effective amount of a compound of the application or a pharmaceutically acceptable salt or solvate thereof.

The application provides a method of treating and/or preventing tachy-arrhythmias in a subject comprising administering to the subject in need thereof an effective amount of a compound of the application or a pharmaceutically acceptable salt or solvate thereof.

In one embodiment, a compound of the application is useful in the amelioration of an inflammatory disorder, for example in the treatment of a skin condition (e.g., sunburn, burns, eczema, dermatitis, psoriasis); ophthalmic disease; a lung disorder (e.g., asthma, bronchitis, emphysema, allergic rhinitis, non-allergic rhinitis, cough, respiratory distress syndrome, pigeon fancier's disease, farmer's lung, chronic obstructive pulmonary disease, (COPD); a gastrointestinal tract disorder (e.g., Crohn's disease, ulcerative colitis, coeliac disease, regional ileitis, irritable bowel syndrome, inflammatory bowel disease, gastroesophageal reflux disease); other conditions with an inflammatory component such as migraine, multiple sclerosis, myocardial ischemia.

In one embodiment, a compound of the application is useful in the treatment of bladder hyperrelexia following bladder inflammation.

In one embodiment, a compound of the application is useful in the treatment of a neurodegenerative disease or neurodegeneration such as dementia, particularly degenerative dementia (including senile dementia, Alzheimer's disease, Pick's disease, Huntington's chorea, Parkinson's disease and Creutzfeldt-Jakob disease, motor neuron disease). In one embodiment, a compound of the application is useful for the treatment of amyotrophic lateral sclerosis (ALS) or neuro-inflammation.

Combinations

The application also provides the use of a compound of the application in combination with one or more additional therapeutic agents for use in the treatment and/or prevention of conditions and disorders.

It will be appreciated that for the treatment of depression or anxiety, a compound of the application may be used in conjunction with other anti-depressant or anti-anxiety agents, such as norepinephrine reuptake inhibitors, selective serotonin reuptake inhibitors (SSRIs), monoamine oxidase inhibitors (MAOIs), reversible inhibitors of monoamine oxidase (RJMAs), serotonin and noradrenaline reuptake inhibitors (SNRIs), D-adrenoreceptor antagonists, atypical antidepressants, benzodiazepines, 5-$HT_{1A}$ agonists or antagonists, especially 5-$HT_{1A}$ partial agonists, neurokinin-1 receptor antagonists, corticotropin releasing factor (CRF) antagonists, or pharmaceutically acceptable salts thereof.

In one embodiment, a compound of the application is used in combination with one or more of the following agents to treat or prevent bipolar disease: i) mood stabilizers; ii) antipsychotics; and/or iii) antidepressants.

In one embodiment, a compound of the application is used in combination with one or more of the following agents to treat or prevent anxiety disorders: i) anxiolytics; and/or ii) antidepressants.

In one embodiment, a compound of the application is used in combination with one or more of the following agents to improve nicotine withdrawal and reduce nicotine craving: i) nicotine replacement therapy for example a sublingual formulation of nicotine beta-cyclodextrin and nicotine patches; and/or ii) bupropion.

In one embodiment, a compound of the application is used in combination with one or more of the following agents to improve alcohol withdrawal and reduce alcohol craving: i) NMDA receptor antagonists for example acamprosate; ii) GABA receptor agonists for example tetrabamate; and/or iii) Opioid receptor antagonists for example naltrexone.

In one embodiment, a compound of the application is used in combination with one or more of the following agents to improve opiate withdrawal and reduce opiate craving: i) opioid mu receptor agonist/opioid kappa receptor antagonist for example buprenorphine; ii) opioid receptor antagonists for example naltrexone; and/or iii) vasodilatory antihypertensives for example lofexidine.

In one embodiment, a compound of the application is used in combination with one or more of the following agents to treat or prevent sleeping disorders: i) benzodiazepines for example temazepam, lormetazepam, estazolam and triazolam; ii) non-benzodiazepine hypnotics for example zolpidem, zopiclone, zaleplon and indiplon; iii) barbiturates for example aprobarbital, butabarbital, pentobarbital, secobarbita and phenobarbital; iv) antidepressants; and/or v) other sedative-hypnotics for example chloral hydrate and chlormethiazole.

In one embodiment, a compound of the application is used in combination with one or more of the following agents to treat anorexia: i) appetite stimulants for example cyproheptidine; ii) antidepressants; iii) antipsychotics; iv) zinc; and/or v) premenstrual agents for example pyridoxine and progesterones.

In one embodiment, a compound of the application is used in combination with one or more of the following agents to treat or prevent bulimia: i) antidepressants; ii) opioid receptor antagonists; iii) antiemetics for example ondansetron; iv) testosterone receptor antagonists for example flutamide; v) mood stabilisers; vi) zinc; and/or vii) premenstrual agents.

In one embodiment, a compound of the application is used in combination with one or more of the following agents to treat or prevent autism: i) antipsychotics; ii) antidepressants; iii) anxiolytics; and/or iv) stimulants for example methylphenidate, amphetamine formulations and pemoline.

In one embodiment, a compound of the application is used in combination with one or more of the following agents to treat or prevent ADHD: i) stimulants for example methylphenidate, amphetamine formulations and pemoline; and ii) non-stimulants for example norepinephrine reuptake inhibitors (such as atomoxetine), alpha 2 adrenoceptor agonists (such as clonidine), antidepressants, modafinil, and cholinesterase inhibitors (such as galantamine and donezepil).

In one embodiment, a compound of the application is used in combination with one or more of the following agents to treat personality disorders: i) antipsychotics; ii) antidepressants; iii) mood stabilisers; and/or iv) anxiolytics.

In one embodiment, a compound of the application is used in combination with one or more of the following agents to treat or prevent male sexual dysfunction: i) phosphodiesterase V inhibitors, for example vardenafil and sildenafil; ii) dopamine agonists/dopamine transport inhibitors for example apomorphine and buproprion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine and/or vii) 5-HT1A agonists, for example flibanserine.

In one embodiment, a compound of the application is be used in combination with one or more of the same agents specified for male sexual dysfunction to treat or prevent female sexual dysfunction, and in addition an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone and amisulpride).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabilizer drugs include lithium, sodium valproate/valproic acid/divalproex, carbamazepine, lamotrigine, gabapentin, topiramate and tiagabine.

Anxiolytics include benzodiazepines such as alprazolam and lorazepam.

A compound of the application may be administered as the raw chemical but the active ingredient is preferably presented as a pharmaceutical formulation.

According to a further aspect, the application provides a pharmaceutical composition comprising a compound of the application, in association with one or more pharmaceutically acceptable carrier(s), diluents(s) and/or excipient(s).

The carrier, diluent and/or excipient must be "acceptable" in the sense of being compatible with the other ingredients of the composition and not deleterious to the recipient thereof.

The compounds of the application may be administered in conventional dosage forms prepared by combining a compound of the application with standard pharmaceutical carriers or diluents according to conventional procedures well known in the art. These procedures may involve mixing, granulating and compressing or dissolving the ingredients as appropriate to the desired preparation.

The pharmaceutical compositions of the application may be formulated for administration by any route, and include those in a form adapted for oral, topical or parenteral administration to mammals including humans.

The compositions may be in the form of tablets, capsules, powders, granules, lozenges, creams or liquid preparations, such as oral or sterile parenteral solutions or suspensions.

The topical formulations of the present application may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerin, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g., cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter-sterilized before filling into a suitable vial or ampoule and sealing.

Advantageously, agents such as local anaesthetics, preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% by weight, for example from 10-60% by weight, of the active material, depending on the method of administration. Where the compositions comprise dosage units, each unit will for example contain from 5-1000 mg of the active ingredient. The dosage as employed for adult human treatment may range from 10 to 3000 mg per day depending on the route and frequency of administration. For oral administration a typical dose may be in the range of 50 to 1500 mg per day, for example 120 to 1000 mg per day.

It will be recognized by one of skill in the art that the optimal quantity and spacing of individual dosages of a compound of the application will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of a compound of the application given per day for a defined number of days, can be ascertained by those skilled in the art using conventional course of treatment determination tests.

In one aspect, the application provides a medical device containing a compound of the application or a pharmaceutically acceptable salt or solvate thereof.

The following Examples are illustrative and should not be interpreted in any way so as to limit the scope of the application.

EXAMPLES

Example 1. Preparation of Compound 1A 2,2,2-trifluoro-1-(2-fluorophenyl)ethyl trifluoromethanesulfonate

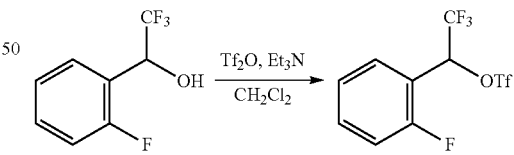

Under nitrogen, to 2,2,2-trifluoro-1-(2-fluorophenyl)ethanol (2.2 g, 11 mmol, 1.0 equiv) in $CH_2Cl_2$ (11 mL) at 0° C. was added triethylamine (2.4 µM, 17 mmol, 1.5 equiv) and $Tf_2O$ (2.9 µM, 17 mmol, 1.5 equiv). After stirring for 2 hr at 23° C., triethylamine (2.4 µM, 17 mmol, 1.5 equiv) and $Tf_2O$ (2.9 µM, 17 mmol, 1.5 equiv) was added and the reaction mixture was further stirred for 1 hr at 23° C. To the reaction mixture was added 1N NaOH (aq) (10 mL), the phases were separated, and the aqueous phase was extracted with $CH_2Cl_2$ (2×10 mL). The combined organic phases were washed with brine (10 mL) and dried ($MgSO_4$). The filtrate was concentrated in vacuo and the residue was purified by column chromatography on silica gel eluting with hexanes/EtOAc to afford 1.0 g of the title compound (27% yield).

NMR Spectroscopy: $^1$H NMR (300 MHz, CDCl$_3$, 23° C., δ): 7.64-7.50 (m, 2H), 7.31 (dd, J=4.8 Hz, 4.8 Hz, 1H), 7.20 (dd, J=9.0 Hz, 8.7 Hz, 1H), 6.29 (q, J=5.7 Hz, 1H). $^{19}$F NMR (282 MHz, CDCl$_3$, 23° C., δ): −74.5 (s, 3F), −76.5 (s, 3F), −116.7 (m, 1F).

1-(1-(4-bromophenoxy)-2,2,2-trifluoroethyl)-2-fluorobenzene

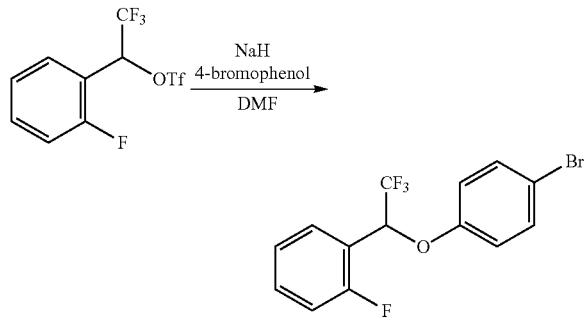

Under nitrogen, to 2,2,2-trifluoro-1-(2-fluorophenyl)ethyl trifluoromethanesulfonate (1.0 g, 3.1 mmol, 1.0 equiv) in DMF (3.1 mL) at 23° C. was added NaH (81 mg, 3.4 mmol, 1.1 equiv) and 4-bromophenol (558 mg, 3.22 mmol, 1.05 equiv). After stirring for 30 min at 70° C., water (10 mL) was added to the reaction mixture. The phases were separated and the aqueous phase was extracted with Et$_2$O (3×10 mL). The combined organic phases were washed with brine (10 mL) and dried (MgSO$_4$). The filtrate was concentrated in vacuo and the residue was purified by column chromatography on silica gel eluting with hexanes/EtOAc to afford 750 mg of the title compound (70% yield).

NMR Spectroscopy: $^1$H NMR (300 MHz, CDCl$_3$, 23° C., δ): 7.58 (dd, J=7.5 Hz, 7.2 Hz, 1H), 7.44-7.32 (m, 3H), 7.22-7.10 (m, 2H), 6.78 (d, J=9.0 Hz, 2H), 5.79 (q, J=6.0 Hz, 1H). $^{19}$F NMR (282 MHz, CDCl$_3$, 23° C., δ): −76.9 (s, 3F), −118.0 (m, 1F).

(2S)-methyl 2-((tert-butoxycarbonyl)amino)-5-oxo-5-(4-(2,2,2-trifluoro-1-(2-fluorophenyl)ethoxy)phenyl)pentanoate

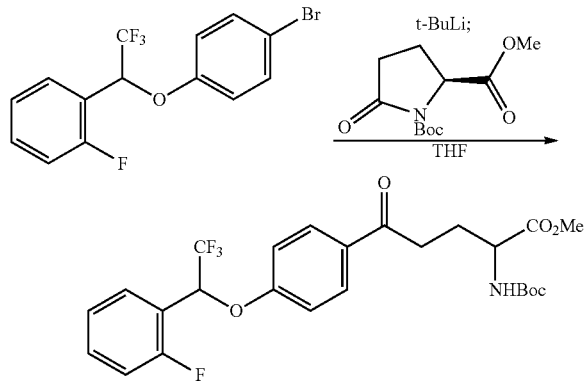

Under nitrogen, to 1-(1-(4-bromophenoxy)-2,2,2-trifluoroethyl)-2-fluorobenzene (1.06 g, 3.04 mmol, 1.20 equiv) in THF (15 mL) at −78° C. was added t-BuLi (1.7 M in pentane, 3.7 mL, 6.3 mmol, 2.5 equiv). After stirring for 1 hr at −78° C., (S)-methyl-N-Boc-pyroglutamate (616 mg, 2.53 mmol, 1.00 equiv) in THF (5 mL) was added and the reaction mixture was stirred for 30 min at −78° C. To the reaction mixture was added i-PrOH (0.5 mL), warmed up to 23° C., and NH$_4$Cl (aq) (20 mL) was added. The phases were separated and the aqueous phase was extracted with EtOAc (3×15 mL). The combined organic phases were washed with brine (30 mL) and dried (MgSO$_4$). The filtrate was concentrated in vacuo and the residue was purified by column chromatography on silica gel eluting with hexanes/EtOAc to afford 910 mg of the title compound (70% yield).

NMR Spectroscopy: $^1$H NMR (300 MHz, CDCl$_3$, 23° C., δ): 7.88 (d, J=9.0 Hz, 2H), 7.56 (dd, J=7.5 Hz, 7.2 Hz, 1H), 7.45-7.38 (m, 1H), 7.22-7.16 (m, 2H), 6.94 (d, J=9.0 Hz, 2H), 5.93 (q, J=6.0 Hz, 1H), 5.15-5.08 (m, 1H), 4.40-4.29 (m, 1H), 3.73 (s, 3H), 3.10-2.83 (m, 2H), 2.32-1.99 (m, 2H), 1.40 (s, 9H). $^{19}$F NMR (282 MHz, CDCl$_3$, 23° C., δ): −76.8 (s, 3F), −117.9 (m, 1F).

(2S,5R)-methyl 5-(4-(2,2,2-trifluoro-1-(2-fluorophenyl)ethoxy)phenyl)pyrrolidine-2-carboxylate

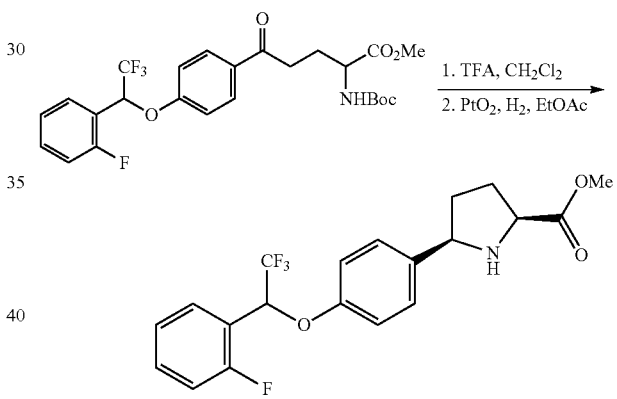

Under nitrogen, to (2S)-methyl 2-((tert-butoxycarbonyl)amino)-5-oxo-5-(4-(2,2,2-trifluoro-1-(2-fluorophenyl)ethoxy)phenyl)pentanoate (910 mg, 1.77 mmol, 1.00 equiv) in CH$_2$Cl$_2$ (3 mL) at 23° C. was added TFA (3.0 mL). After stirring for 30 min at 23° C., the reaction mixture was concentrated to afford a crude imine, which was used in the following step without further purification.

Under air, to the above obtained crude imine in EtOAc (9.0 mL) at 23° C. was added PtO$_2$ (24 mg, 011 mmol, 6.0 mol %) and H$_2$ gas was introduced with a balloon. After stirring for 3 hr at 70° C., the reaction mixture was cooled to 23° C. and K$_2$CO$_3$ (aq) (10 mL) was added. The phases were separated and the aqueous phase was extracted with EtOAc (3×15 mL). The combined organic phases were washed with brine (30 mL), dried (MgSO$_4$), and filtered through a pad of celite. The filtrate was concentrated in vacuo and the residue was purified by column chromatography on silica gel eluting with hexanes/EtOAc to afford 534 mg of the title compound (76% yield, 2 steps).

NMR Spectroscopy: $^1$H NMR (300 MHz, CDCl$_3$, 23° C., δ): 7.61 (dd, J=7.8 Hz, 7.2 Hz, 1H), 7.45-7.38 (m, 3H), 7.21-7.10 (m, 2H), 6.85 (d, J=9.0 Hz, 2H), 5.83 (q, J=6.0 Hz, 1H), 4.15-4.08 (m, 1H), 3.92-3.83 (m, 1H), 3.75 (s, 3H), 2.22-2.04 (m, 3H), 1.64-1.58 (m, 1H). $^{19}$F NMR (282 MHz, CDCl$_3$, 23° C., δ): −76.9 (s, 3F), −118.0 (m, 1F).

(2S,5R)-5-(4-(2,2,2-trifluoro-1-(2-fluorophenyl)ethoxy)phenyl)pyrrolidine-2-carboxamide

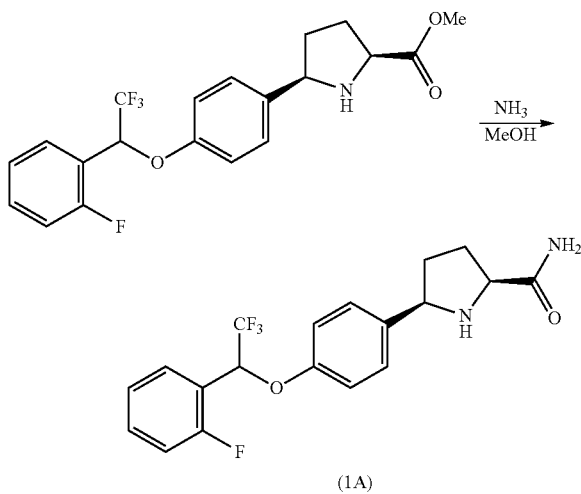

Under nitrogen, to (2S,5R)-methyl 5-(4-(2,2,2-trifluoro-1-(2-fluorophenyl)ethoxy)phenyl)pyrrolidine-2-carboxylate (119 mg, 0.300 mmol, 1.00 equiv) at 23° C. was added 7 M NH$_3$ in MeOH (1.5 mL). After stirring for 5 hr and 27 hr at 23° C., 7 M NH$_3$ in MeOH (1.5 mL) was added, respectively. After stirring for another 5 hr at 23° C., the reaction mixture was concentrated in vacuo and the residue was purified by column chromatography on silica gel eluting with CH$_2$Cl$_2$/MeOH to afford 89 mg of the title compound as colorless solid (78%).

NMR Spectroscopy: $^1$H NMR (300 MHz, CDCl$_3$, 23° C., δ): 7.62 (dd, J=7.8 Hz, 7.2 Hz, 1H), 7.49-7.38 (m, 2H), 7.29-7.10 (m, 4H), 6.87 (d, J=9.0 Hz, 2H), 5.97 (br s, 1H), 5.83 (q, J=6.0 Hz, 1H), 4.24 (dd, J=10.2 Hz, 6.0 Hz, 1H), 3.83 (dd, J=10.2 Hz, 3.9 Hz, 1H), 2.42 (br s, 1H), 2.36-2.02 (m, 3H), 1.68-1.50 (m, 1H). $^{19}$F NMR (282 MHz, CDCl$_3$, 23° C., δ): −76.9 (s, 3F), −118.0 (m, 1F).

Example 2: Preparation of Compound 2A 5-bromo-2-((2-fluorobenzyl)oxy)pyridine

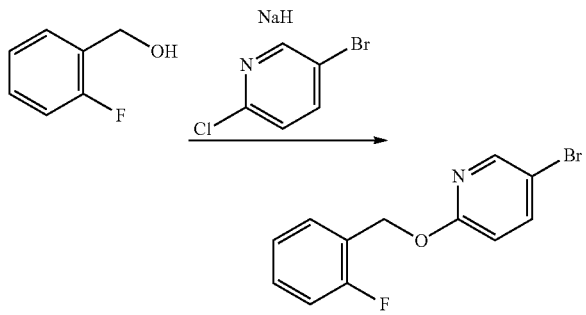

Under nitrogen, to 2-fluorobenzylalcohol (1.64 g, 13.0 mmol, 1.30 equiv) in DMF (5 mL) at 0° C. was added NaH (299 mg, 13.0 mmol, 1.30 equiv). After stirring for 5 min at 23° C., 5-bromo-2-chloropyridine (1.92 g, 10.0 mmol, 1.00 equiv) was added. After further stirring for 20 min at 85° C., water (20 mL) was added to the reaction mixture. The phases were separated and the aqueous phase was extracted with Et$_2$O (3×20 mL). The combined organic phases were washed with brine (20 mL) and dried (MgSO$_4$). The filtrate was concentrated in vacuo and the residue was purified by column chromatography on silica gel eluting with hexanes/EtOAc to afford 2.6 g of the title compound (92% yield).

NMR Spectroscopy: $^1$H NMR (400 MHz, CDCl$_3$, 23° C., δ): 8.21 (br s, 1H), 7.66 (d, J=8.8 Hz, 1H), 7.50-7.42 (m, 1H), 7.35-7.28 (m, 1H), 7.18-7.06 (m, 2H), 6.73 (d, J=8.8 Hz, 1H), 5.42 (s, 2H). $^{19}$F NMR (375 MHz, CDCl$_3$, 23° C., δ): −118.2 (m, 1F).

(S)-methyl 2-((tert-butoxycarbonyl)amino)-5-(6-((2-fluorobenzyl)oxy)pyridin-3-yl)-5-oxopentanoate

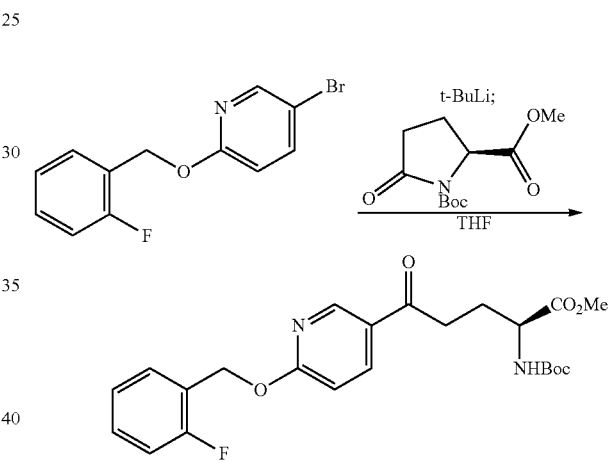

Under nitrogen, to 5-bromo-2-((2-fluorobenzyl)oxy)pyridine (100 mg, 0.355 mmol, 1.00 equiv) in THF (1.8 mL) at −78° C. was added t-BuLi (1.7 M in pentane, 0.42 mL, 0.71 mmol, 2.0 equiv). After stirring for 30 min at −78° C., (S)-methyl-N-Boc-pyroglutamate (86 mg, 0.35 mmol, 1.0 equiv) in THF (0.6 mL) was added and the reaction mixture was stirred for 30 min at −78° C. To the reaction mixture was added i-PrOH (0.2 mL), warmed up to 23° C., and NH$_4$Cl (aq) (5 mL) was added. The phases were separated and the aqueous phase was extracted with EtOAc (3×5 mL). The combined organic phases were washed with brine (10 mL) and dried (MgSO$_4$). The filtrate was concentrated in vacuo and the residue was purified by column chromatography on silica gel eluting with hexanes/EtOAc to afford 100 mg of the title compound (63% yield). NMR Spectroscopy: $^1$H NMR (400 MHz, CDCl$_3$, 23° C., δ): 8.80 (br s, 1H), 8.15 (d, J=8.4 Hz, 1H), 7.49 (dd, J=7.6 Hz, 7.2 Hz, 1H), 7.39-7.28 (m, 1H), 7.18-7.06 (m, 2H), 6.84 (d, J=8.4 Hz, 1H), 5.52 (s, 2H), 5.18-5.12 (m, 1H), 4.44-4.36 (m, 1H), 3.75 (s, 3H), 3.13-2.93 (m, 2H), 2.38-2.02 (m, 2H), 1.42 (s, 9H). $^{19}$F NMR (375 MHz, CDCl$_3$, 23° C., δ): −118.1 (m, 1F).

(2S,5R)-5-(6-((2-fluorobenzyl)oxy)pyridin-3-yl)pyrrolidine-2-carboxamide

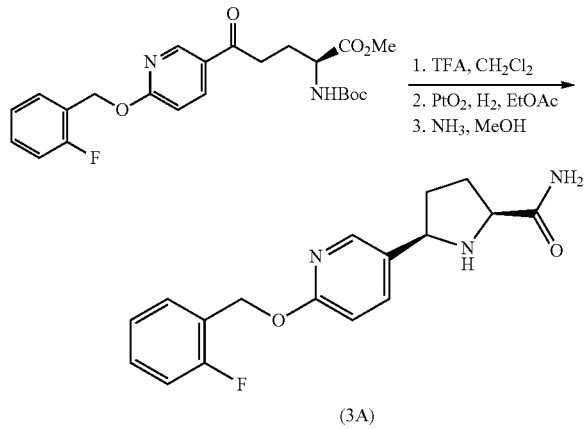

(3A)

Under nitrogen, to (S)-methyl 2-((tert-butoxycarbonyl)amino)-5-(6-((2-fluorobenzyl)oxy)pyridin-3-yl)-5-oxopentanoate (470 mg, 1.05 mmol, 1.00 equiv) in CH$_2$Cl$_2$ (3 mL) at 23° C. was added TFA (3.0 mL). After stirring for 20 min at 23° C., the reaction mixture was concentrated in vacuo to afford a crude imine, which was used in the following step without further purification.

Under air, to the above obtained crude imine in EtOAc (9.0 mL) at 23° C. was added PtO$_2$ (24 mg, 011 mmol, 10 mol %) and H$_2$ gas was introduced with a balloon. After stirring for 3 hr at 23° C., NaHCO$_3$ (aq) (10 mL) was added to the reaction mixture. The phases were separated and the aqueous phase was extracted with EtOAc (3×10 mL). The combined organic phases were washed with brine (20 mL), dried (MgSO$_4$), and filtered through a pad of celite. The filtrate was concentrated in vacuo to afford a crude amine, which was used in the following step without further purification.

Under nitrogen, to the above obtained crude amine at 23° C. was added 7 M NH$_3$ in MeOH (3 mL). After stirring for 23 hr at 65° C., the reaction mixture was concentrated in vacuo and the residue was purified by column chromatography on silica gel eluting with CH$_2$Cl$_2$/MeOH to afford 23 mg of the title compound as colorless solid (7%, 3 steps).

NMR Spectroscopy: $^1$H NMR (400 MHz, CDCl$_3$, 23° C., δ): 8.16 (br s, 1H), 7.63 (d, J=8.4 Hz, 1H), 7.52-7.38 (m, 2H), 7.35-7.05 (m, 3H), 6.80 (d, J=8.4 Hz, 1H), 5.79 (br s, 1H), 5.44 (s, 2H), 4.31 (dd, J=10.2 Hz, 6.0 Hz, 1H), 3.87 (dd, J=10.2 Hz, 3.9 Hz, 1H), 2.55 (br s, 1H), 2.38-2.02 (m, 3H), 1.72-1.60 (m, 1H). $^{19}$F NMR (375 MHz, CDCl$_3$, 23° C., δ): -118.3 (m, 1F).

Example 3. Preparation of Compound 3A 5-bromo-2-(2,2,2-trifluoro-1-(2-fluorophenyl)ethoxy)pyridine

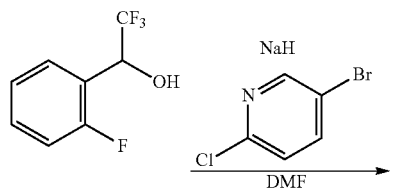

Under nitrogen, to 2,2,2-trifluoro-1-(2-fluorophenyl)ethanol (3.4 g, 18 mmol, 1.3 equiv) in DMF (14 mL) at 0° C. was added NaH (403 mg, 17.5 mmol, 1.30 equiv). After stirring for 10 min at 23° C., 5-bromo-2-chloropyridine (2.59 g, 13.5 mmol, 1.00 equiv) was added. After further stirring for 2 hr at 85° C., water (20 mL) was added to the reaction mixture. The phases were separated and the aqueous phase was extracted with EOAc (3×20 mL). The combined organic phases were washed with brine (20 mL) and dried (MgSO$_4$). The filtrate was concentrated in vacuo and the residue was purified by column chromatography on silica gel eluting with hexanes/EtOAc to afford 1.56 g of the title compound (33% yield).

NMR Spectroscopy: $^1$H NMR (400 MHz, CDCl$_3$, 23° C., δ): 8.12 (br s, 1H), 7.72 (d, J=8.8 Hz, 1H), 7.57 (dd, J=7.6 Hz, 7.6 Hz, 1H), 7.40-7.32 (m, 1H), 7.18-7.06 (m, 2H), 6.90 (q, J=6.0 Hz, 1H), 6.84 (d, J=8.8 Hz, 1H). $^{19}$F NMR (375 MHz, CDCl$_3$, 23° C., δ): -76.4 (s, 3F), -116.7 (m, 1F).

(2S)-methyl 2-((tert-butoxycarbonyl)amino)-5-oxo-5-(6-(2,2,2-trifluoro-1-(2-fluorophenyl)ethoxy)pyridin-3-yl)pentanoate

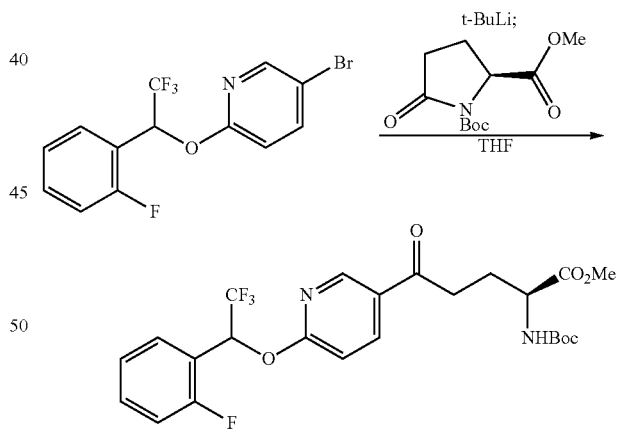

Under nitrogen, to 5-bromo-2-((2-fluorobenzyl)oxy)pyridine (700 mg, 2.00 mmol, 1.00 equiv) in THF (10 mL) at -78° C. was added t-BuLi (1.7 M in pentane, 2.4 mL, 4.0 mmol, 2.0 equiv). After stirring for 5 min at -78° C., (S)-methyl-N-Boc-pyroglutamate (487 mg, 2.00 mmol, 1.00 equiv) in THF (2 mL) was added and the reaction mixture was stirred for 15 min at -78° C. To the reaction mixture was added i-PrOH (0.5 mL), warmed up to 23° C., and NH$_4$Cl (aq) (15 mL) was added. The phases were separated and the aqueous phase was extracted with EtOAc (3×10 mL). The combined organic phases were washed with brine (10 mL)

and dried (MgSO$_4$). The filtrate was concentrated in vacuo and the residue was purified by column chromatography on silica gel eluting with hexanes/EtOAc to afford 630 mg of the title compound (61% yield).

NMR Spectroscopy: $^1$H NMR (400 MHz, CDCl$_3$, 23° C., δ): 8.68 (br s, 1H), 8.19 (d, J=8.4 Hz, 1H), 7.58 (dd, J=7.6 Hz, 7.2 Hz, 1H), 7.40-7.32 (m, 1H), 7.19-6.99 (m, 4H), 5.16-5.08 (m, 1H), 4.41-4.32 (m, 1H), 3.73 (s, 3H), 3.10-2.89 (m, 2H), 2.36-2.00 (m, 2H), 1.39 (s, 9H). $^{19}$F NMR (375 MHz, CDCl$_3$, 23° C., δ): -76.3 (s, 3F), -116.7 (m, 1F).

(2S,5R)-5-(6-(2,2,2-trifluoro-1-(2-fluorophenyl)ethoxy)pyridin-3-yl)pyrrolidine-2-carboxamide

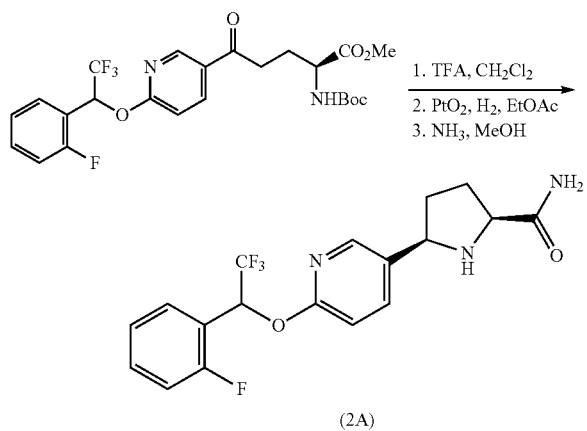

(2A)

Under nitrogen, to (2,9-methyl 2-((tert-butoxycarbonyl)amino)-5-oxo-5-(6-(2,2,2-trifluoro-1-(2-fluorophenyl)ethoxy)pyridin-3-yl)pentanoate (630 mg, 1.22 mmol, 1.00 equiv) in CH$_2$Cl$_2$ (3 mL) at 23° C. was added TFA (3.0 mL). After stirring for 20 min at 23° C., the reaction mixture was concentrated in vacuo to afford a crude imine, which was used in the following step without further purification.

Under air, to the above obtained crude imine in EtOAc (9.0 mL) at 23° C. was added PtO$_2$ (28 mg, 012 mmol, 10 mol %) and H$_2$ gas was introduced with a balloon. After stirring for 3 hr at 23° C., NaHCO$_3$ (aq) (10 mL) was added to the reaction mixture. The phases were separated and the aqueous phase was extracted with EtOAc (3×10 mL). The combined organic phases were washed with brine (20 mL), dried (MgSO$_4$), and filtered through a pad of celite. The filtrate was concentrated in vacuo to afford a crude amine, which was used in the following step without further purification.

Under nitrogen, to the above obtained crude amine at 23° C. was added 7 M NH$_3$ in MeOH (3 mL). After stirring for 23 hr at 65° C., the reaction mixture was concentrated in vacuo and the residue was purified by column chromatography on silica gel eluting with CH$_2$Cl$_2$/MeOH to afford 100 mg of the title compound as colorless solid (21%, 3 steps).

$^1$H NMR (400 MHz, CDCl$_3$, 23° C., δ): 8.07 (br s, 1H), 7.68-7.58 (m, 2H), 7.41-7.32 (m, 2H), 7.20-7.07 (m, 2H), 7.00 (q, J=6.0 Hz, 1H), 6.90 (d, J=8.4 Hz, 2H), 5.57 (br s, 1H), 4.26 (dd, J=10.2 Hz, 6.0 Hz, 1H), 3.84 (dd, J=10.2 Hz, 3.9 Hz, 1H), 2.55 (br s, 1H), 2.36-2.04 (m, 3H), 1.69-1.57 (m, 1H). $^{19}$F NMR (375 MHz, CDCl$_3$, 23° C., δ): -76.4 (s, 3F), -116.8 (m, 1F).

Example 4: Preparing Diastereomers of the Compounds of the Application (9-methyl 5-(4-hydroxyphenyl)-3,4-dihydro-2H-pyrrole-2-carboxylate

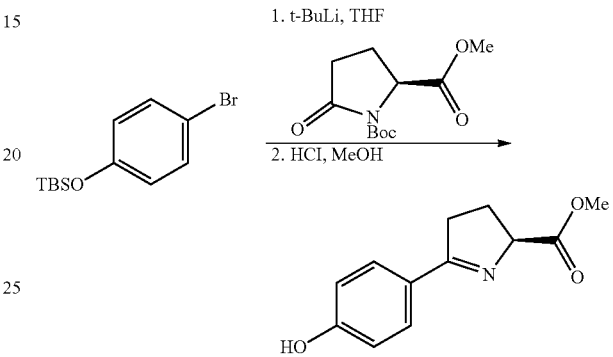

Under nitrogen, to (4-bromophenoxy)(tert-butyl)dimethylsilane (1.70 g, 5.92 mmol, 1.00 equiv) in THF (30 mL) at -78° C. was added t-BuLi (1.7 M in pentane, 7.0 mL, 12 mmol, 2.0 equiv). After stirring for 1 hr at -78° C., (9-methyl-N-Boc-pyroglutamate (1.44 g, 5.92 mmol, 1.00 equiv) in THF (10 mL) was added and the reaction mixture was stirred for 30 min at -78° C. To the reaction mixture was added i-PrOH (0.5 mL), warmed up to 23° C., and NH$_4$Cl (aq) (40 mL) was added. The phases were separated and the aqueous phase was extracted with EtOAc (3×30 mL). The combined organic phases were washed with brine (50 mL) and dried (MgSO$_4$). The filtrate was concentrated in vacuo and the residue was purified by column chromatography on silica gel eluting with hexanes/EtOAc to afford 440 mg of the addition product. The compound appeared to be a mixture of diastereomers and was used in the next step without further structural analysis.

Under nitrogen, to the compound obtained above in MeOH (3 mL) was added 2M HCl in Et$_2$O (2.5 mL, 5.0 mmol, 5.0 equiv). After being stirred for 9 hr at 50° C., the reaction mixture was concentrated in vacuo, and EtOAc (10 mL) along with NaHCO$_3$ (aq) (10 mL) was added to the residue. The phases were separated and the aqueous phase was extracted with EtOAc (3×10 mL). The combined organic phases were washed with brine (20 mL) and dried (MgSO$_4$). The filtrate was concentrated in vacuo and the residue was purified by column chromatography on silica gel eluting with hexanes/EtOAc to afford 159 mg of (S)-methyl 5-(4-hydroxyphenyl)-3,4-dihydro-2H-pyrrole-2-carboxylate (12% yield, 2 steps).

$^1$H NMR (300 MHz, CDCl$_3$, 23° C., δ): 7.71 (d, J=6.6 Hz, 2H), 6.77 (d, J=6.6 Hz, 2H), 4.90 (dd, J=5.1 Hz, 5.1 Hz, 1H), 3.75 (s, 3H), 3.20-2.90 (m, 2H), 2.41-2.20 (m, 2H).

(2S)-methyl 5-(4-(2,2,2-trifluoro-1-(2-fluorophenyl)ethoxy)phenyl)-3,4-dihydro-2H-pyrrole-2-carboxylate

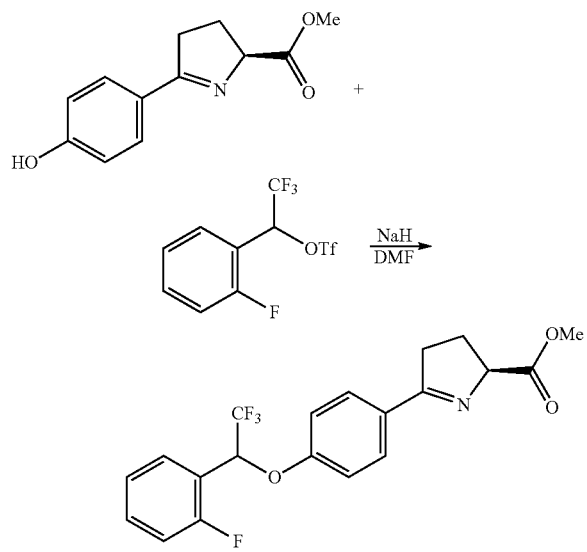

Under nitrogen, to 2,2,2-trifluoro-1-(2-fluorophenyl)ethyl trifluoromethanesulfonate (307 mg, 0.942 mmol, 1.30 equiv) in DMF (2 mL) at 23° C. were added NaH (17 mg, 0.73 mmol, 1.0 equiv) and (S)-methyl 5-(4-hydroxyphenyl)-3,4-dihydro-2H-pyrrole-2-carboxylate (159 mg, 0.725 mmol, 1.00 equiv). After stirring for 1 hr at 23° C., water (5 mL) was added to the reaction mixture. The phases were separated and the aqueous phase was extracted with EtOAc (3×5 mL). The combined organic phases were washed with brine (10 mL) and dried (MgSO$_4$). The filtrate was concentrated in vacuo and the residue was purified by column chromatography on silica gel eluting with hexanes/EtOAc to afford 210 mg of (2S)-methyl 5-(4-(2,2,2-trifluoro-1-(2-fluorophenyl)ethoxy)phenyl)-3,4-dihydro-2H-pyrrole-2-carboxylate (73% yield).

$^1$H NMR (300 MHz, CDCl$_3$, 23° C., δ): 7.78 (d, J=6.6 Hz, 2H), 7.61-7.55 (m, 1H), 7.42-7.37 (m, 1H), 7.20-7.12 (m, 2H), 6.92 (d, J=6.6 Hz, 2H), 5.91 (q, J=6.0 Hz, 1H), 4.87 (dd, J=5.1 Hz, 5.1 Hz, 1H), 3.76 (s, 3H), 3.14-2.84 (m, 2H), 2.38-2.12 (m, 2H). $^{19}$F NMR (282 MHz, CDCl$_3$, 23° C., δ): −76.8 (s, 3F), −117.9 (m, 1F).

(2S,5R)-methyl 5-(4-(2,2,2-trifluoro-1-(2-fluorophenyl)ethoxy)phenyl)pyrrolidine-2-carboxylate

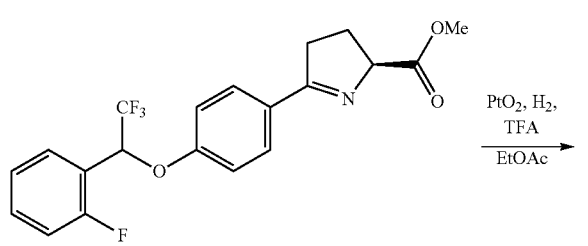

Under air, to (2S)-methyl 5-(4-(2,2,2-trifluoro-1-(2-fluorophenyl)ethoxy)phenyl)-3,4-dihydro-2H-pyrrole-2-carboxylate (210 mg, 0.531 mmol, 1.00 equiv) in EtOAc (5.0 mL) at 23° C. were added TFA (41 μL, 0.53 mmol, 1.0 equiv) and PtO$_2$ (12 mg, 0.053 mmol, 10 mol %), and H$_2$ gas was introduced with a balloon. After stirring for 3 hr at 70° C., the reaction mixture was cooled to 23° C. and K$_2$CO$_3$ (aq) (5 mL) was added. The phases were separated and the aqueous phase was extracted with EtOAc (3×5 mL). The combined organic phases were washed with brine (10 mL), dried (MgSO$_4$), and filtered through a pad of celite. The filtrate was concentrated in vacuo and the residue was purified by column chromatography on silica gel eluting with hexanes/EtOAc to afford 200 mg of (2S,5R)-methyl 5-(4-(2,2,2-trifluoro-1-(2-fluorophenyl)ethoxy)phenyl)pyrrolidine-2-carboxylate (95% yield).

$^1$H NMR (300 MHz, CDCl$_3$, 23° C., δ): 7.61 (dd, J=7.8 Hz, 7.2 Hz, 1H), 7.45-7.38 (m, 3H), 7.21-7.10 (m, 2H), 6.85 (d, J=9.0 Hz, 2H), 5.83 (q, J=6.0 Hz, 1H), 4.15-4.08 (m, 1H), 3.92-3.83 (m, 1H), 3.75 (s, 3H), 2.22-2.04 (m, 3H), 1.64-1.58 (m, 1H). $^{19}$F NMR (282 MHz, CDCl$_3$, 23° C., δ): −76.9 (s, 3F), −118.0 (m, 1F).

Separation of Diastereomers

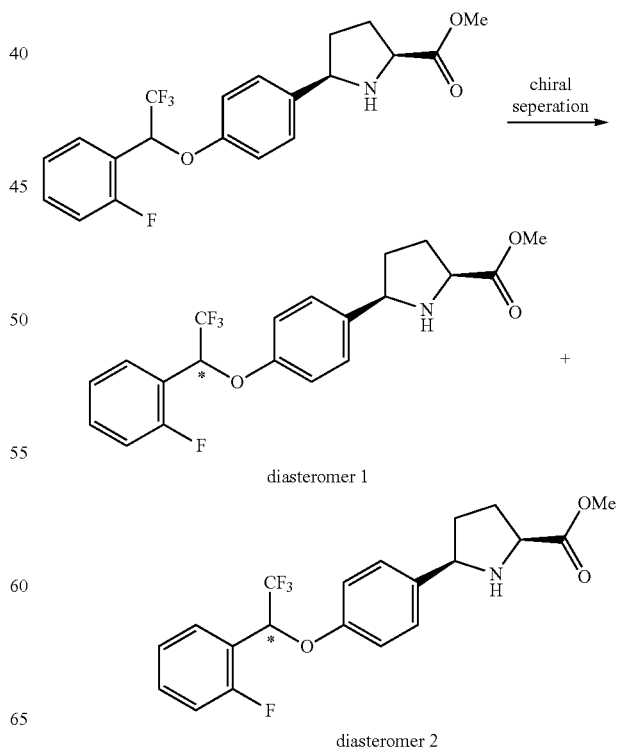

200 mg of (2S,5R)-methyl 5-(4-(2,2,2-trifluoro-1-(2-fluorophenyl)ethoxy)phenyl) pyrrolidine-2-carboxylate synthesized above was subjected to a preparative SFC method described below to obtain 80 mg (100% de) of fast-moving diastereomer and 58 mg (100% de) of slow-moving diastereomer, respectively.

Column: 2.1×25.0 cm (S,S) Whelk0-1 from Regis Technologies (Morton Grove, Ill.)
$CO_2$ Co-solvent (Solvent B): Ethanol with 1% Isopropylamine
Isocratic Method: 16% Co-solvent at 70 mL/min
System Pressure: 100 bar
Column Temperature: 25° C.
Sample Diluent: Ethanol The fractions obtained above were analyzed using an analytical SFC method described below to determine their diastereomeric excess.

Column: 4.6×100 mm (S,S) Whelk0-1 from Regis Technologies (Morton Grove, Ill.)
$CO_2$ Co-solvent (Solvent B): Ethanol with 0.1% Isopropylamine
Isocratic Method: 10% Co-solvent at 4 mL/min
System Pressure: 100 bar
Column Temperature: 25° C.
Sample Diluent: Methanol Each diastereomer was converted to the corresponding amide using the same experimental procedure.

Example 5. Testing of Compounds for Treatment of Pain

In this widely used model, a 5% solution of formaldehyde was injected subcutaneously to mouse or rat paw to produce a biphasic pain response over a test period of 60 minutes. The initial pain response occurred within 10 minutes following subplantar injection of formalin and resulted from direct stimulation of nociceptors. The second phase of pain response occurred after a period of sensitization (quiescent period) during which inflammatory phenomena took place. Pain response scoring included counts per unit of time of reactions to the pain stimulus, such as flinching, licks, twitches, raising or shaking of the injected paw. Compound 1A was tested in this model and found to be active.

Animal
Sixty female SD rats were used in the study.
Quarantine
Animals were quarantined between 3 and 7 days before dosing. The general health of the animals was evaluated by a veterinarian, and complete health checks were performed. Animals with abnormalities were excluded from the study.
Housing
General procedures for animal care and housing were in accordance with standard operating procedures. The rats were kept in laminar flow rooms at constant temperature and humidity with 3 animals in each cage. Animals were housed in polycarbonate cages and in an environmentally monitored, well-ventilated room maintained at a temperature of (22±3° C.) and a relative humidity of 40%-70%. Fluorescent lighting provided illumination approximately 12 hours per day. The bedding material was corn cobs, which was changed twice per week.
Diet and Water
Sterile normal diets were provided to the animals throughout the study period. Animals had free access to irradiation sterilized dry granule food during the entire study period.

Sterile drinking water in a bottle was provided ad libitum during the quarantine and study periods. The bottle and the stopper with attached sipper tube were autoclaved prior to use. Samples of water from the animal facility were analyzed and results of water analysis were reviewed by the veterinarian, or designee, to assure that no known contaminants were present that could interfere with or affect the outcome of studies.

Rats were randomly assigned to respective groups using a computer-generated randomization procedure. The study groups and number of animals per group are shown in Table 2.

TABLE 2

Group and Treatments

| Group | Treatment | Dose (mg/kg) | Route | N |
|---|---|---|---|---|
| 1 | 5% NMP, 5% solutol HS in saline (vehicle) | 0 | P.O. | n = 10 |
| 2 | morphine | 1 | I.P. | n = 10 |
| 3 | Gabapentin (Gab) | 100 | P.O. | n = 10 |
| 4 | Compound 1A | 3 | P.O. | n = 10 |
| 5 | Compound 1A | 10 | P.O. | n = 10 |
| 6 | Compound 1A | 30 | P.O. | n = 10 |

NMP: 1-methyl-2-pyrrlione
Solutol HS: macrogol (15)-hydroxystearate
Induction Procedure 10% formalin solution was diluted 1:1 in distilled water. The final concentration of formalin was 5%. Rats were placed into the clear plexiglass box that was used during testing. Mirrors were placed behind and beside container to ensure that the animals' injected paws were seen from all angles. Animals were allowed to acclimate for 30 minutes.

50 μL of 5% formalin was injected into the dorsal surface of the left hind paw with a 30-gauge needle. Immediately thereafter, the rat was placed in the plexiglass observation cylinder. This time point was defined as the start (0 minutes) of the formalin-model observation period.

Dosing Procedure
Vehicle: 5% NMP, 5% solutol HS in saline
Route: P.O.
Volume: 5 ml/kg
Frequency: Single dose on study day
Dosing Time: 90 min pre formalin injection
Formulation: Take 2.5 mL NMP and 2.5 mL solutol HS into 45 mL normal saline solution, vortex until a uniform solution was achieved.
Positive Drug: Morphine
Route: I.P.
Volume: 5 ml/kg
Frequency: Single dose on study day
Dosing time: 30 minutes pre formalin injection
Formulation: 300 μL morphine hydrochloride injection (10 mg/mL) was diluted into 15 mL normal saline solution. The final concentration of morphine was 0.2 mg/mL (1 mg/kg).
Positive Drug: Gabapentin
Route: P.O.
Volume: 5 ml/kg
Frequency: Single dose on study day
Dosing time: 30 minutes pre formalin injection
Formulation: Dissolve 300 mg gabapentin in 15 mL normal saline solution, vortex until a uniform transparent solution was achieved. The concentration of the solution was 20 mg/mL (100 mg/kg).
Test Compound: Compound 1A
Route: P.O.
Volume: 5 ml/kg
Frequency: Single dose on study day
Dosing time: 90 min prior formalin injection Formulation: Dissolve 150 mg Compound 1A in 25 mL vehicle solution, vortex with slightly sonication until a uniform transparent solution was achieved, the final concentration of the solution was 6 mg/mL (30 mg/kg). The solution was diluted to 0.6 mg/mL (3 mg/kg) and 2 mg/mL (10 mg/kg).

Clinical Observation Procedure

Nociceptive behaviors were quantified by periodical counting the frequency of spontaneous flinches and the duration of lifting, licking, biting and trembling of the injected paw. Animals were individually observed and the behaviors were counted for 5 minutes periods which began at 0 minute and repeated every 5 minutes thereafter for the 60 minutes observation period. Two phases of spontaneous nociceptive behaviors were observed: phase 1 started at 0 minute and lasted up to 10 minutes, and phase 2 began at 20 minutes and lasted up to 60 minutes. The test articles' effect was assessed from the cumulative number and duration of these behaviors in each phase for each rat.

Statistical Analysis

One-way analysis of variance (ANOVA) was applied among the groups, P<0.05 accepted as significant.

Results

Flinching Response

Figure 1B:
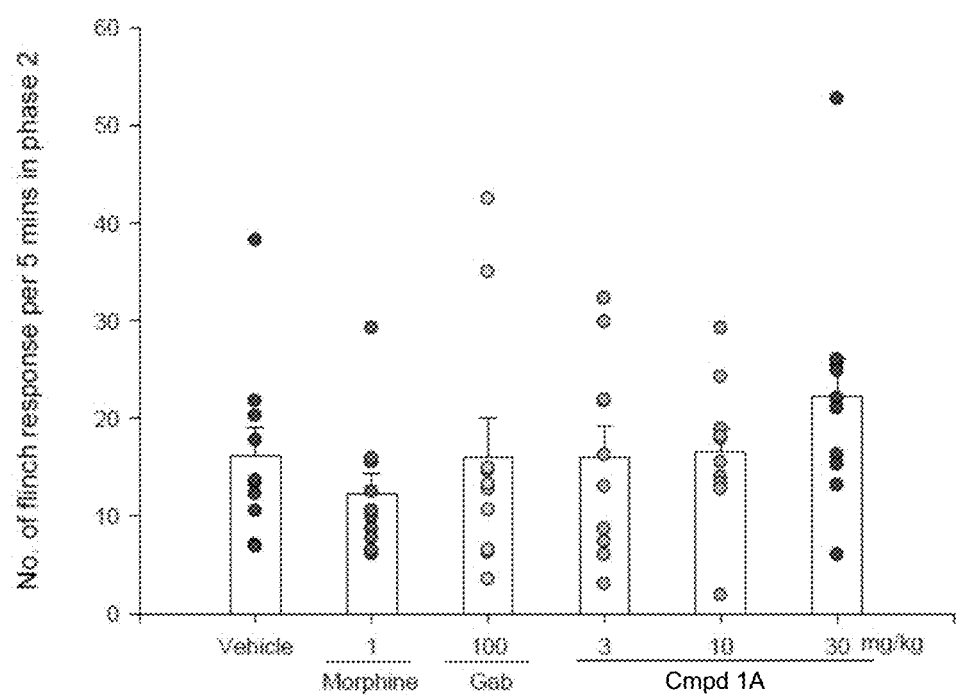
FIG. 1B shows the number of flinching response as a result of formalin induced pain in rats treated with Compound 1A or indicated reagents in the second phase of pain after formalin injection.

Group mean of average flinching response (Ave No/5 min) is shown in Table 3. Effects of Compound 1A on the flinching response in the formalin model are shown in FIGS. 1A and 1B. There was no effect on the flinching response in the groups of Morphine, Gabapentin and Compound 1A at tested dose levels.

TABLE 3

Group Mean of Average Flinching Response (No. per 5 min)

| Group No. | Phase 1 | Phase 2 |
|---|---|---|
| 1 (vehicle) | 22.9 ± 16.7 | 16.2 ± 9.3 |
| 2 (morphine 1 mg/ml) | 10.8 ± 7.7 | 12.3 ± 6.9 |
| 3 (Gab 100 mg/ml) | 11.5 ± 5.7 | 16.0 ± 13.3 |
| 4 (Compound 1A 3 mg/ml) | 15.2 ± 11.3 | 16.0 ± 10.2 |
| 5 (Compound 1A 10 mg/ml) | 10.5 ± 3.7 | 16.6 ± 7.3 |
| 6 (Compound 1A 30 mg/ml) | 22.0 ± 7.7 | 22.3 ± 12.5 |

Duration of Lifting

Figure 2A:
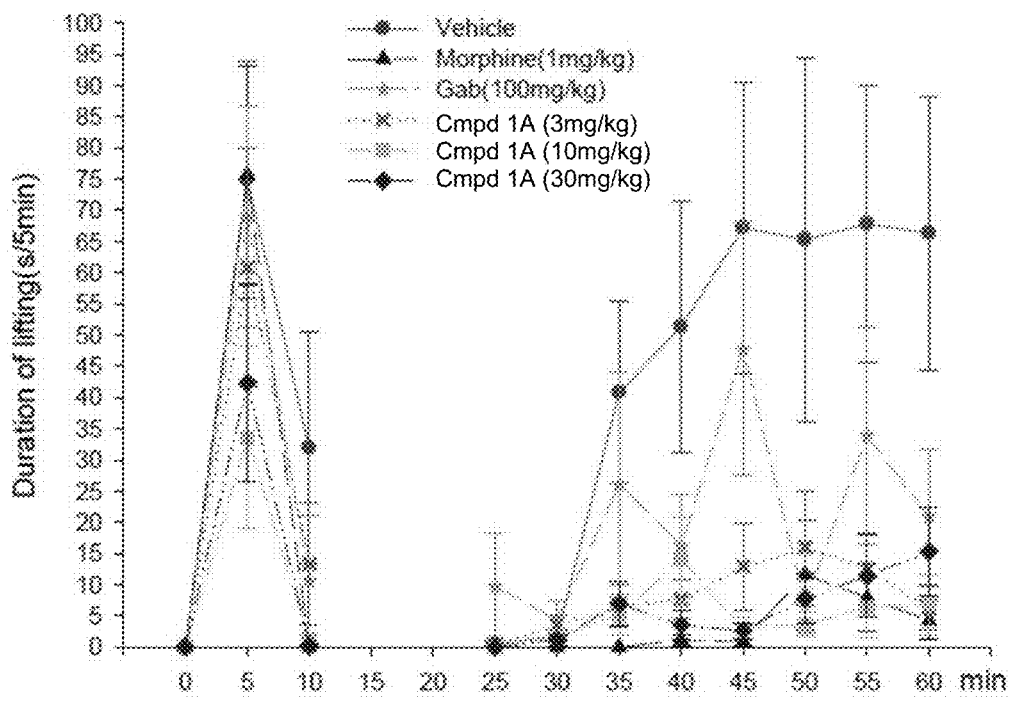
FIG. 2A shows the duration of lifting response as a result of formalin induced pain in rats treated with Compound 1A or indicated reagents during the 60 minutes after formalin injection.
Figure 2B:
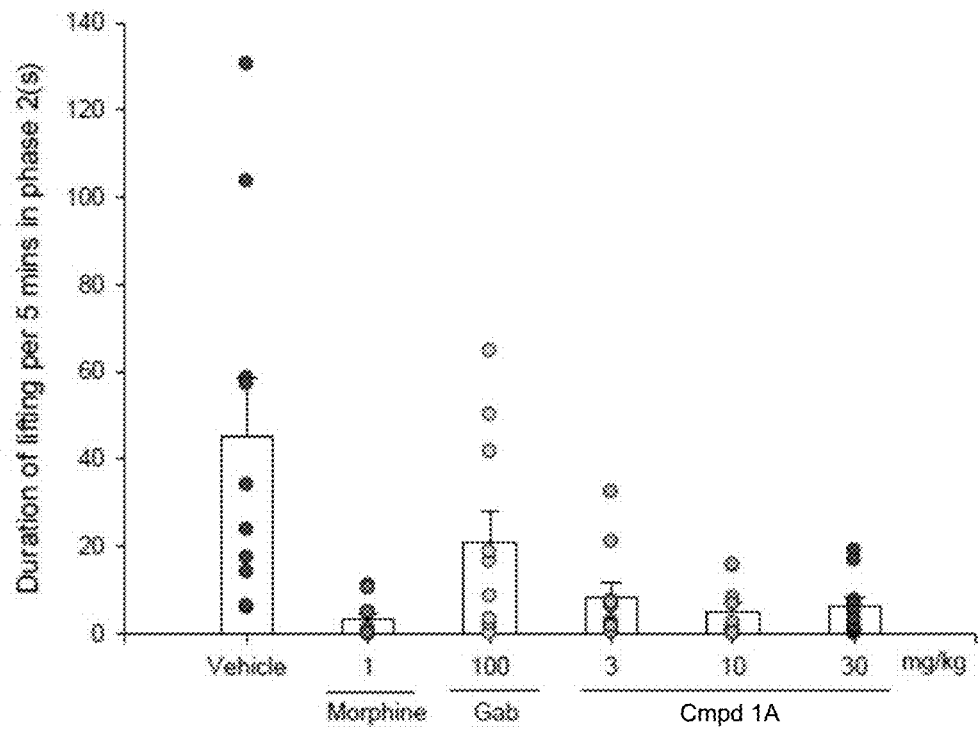
FIG. 2B shows the duration of lifting response as a result of formalin induced pain in rats treated with Compound 1A or indicated reagents in the second phase of pain after formalin injection.

Group mean of average duration of lifting per 5 min is shown in Table 4. Effects of Compound 1A on duration of lifting in the formalin model are shown in FIGS. 2A and 2B. In brief, all test compounds including Morphine, Gabapentin and Compound 1A at all dose levels had significant effect on inhibiting the duration of paw lifting post-formalin injection during the period of phase 2. However, they had no effects during the phase 1 observation period.

TABLE 4

Group Mean of Average Duration of Lifting (No. per 5 min)

| Group No. | Phase 1 | Phase 2 |
|---|---|---|
| 1 (vehicle) | 53.4 ± 55.6 | 45.1 ± 42.7 |
| 2 (morphine 1 mg/ml) | 37.8 ± 27.7 | 3.2 ± 4.4** |
| 3 (Gab 100 mg/ml) | 39.8 ± 41.5 | 20.7 ± 23.2* |
| 4 (Compound 1A 3 mg/ml) | 37.1 ± 43.8 | 8.2 ± 10.4** |
| 5 (Compound 1A 10 mg/ml) | 17.3 ± 22.8 | 5.1 ± 6.2** |
| 6 (Compound 1A 30 mg/ml) | 21.3 ± 25.2 | 6.1 ± 6.7** |

*$p < 0.05$,
**$p < 0.01$, compared with vehicle group

Duration of Licking, Biting and Trembling

Figure 3A:
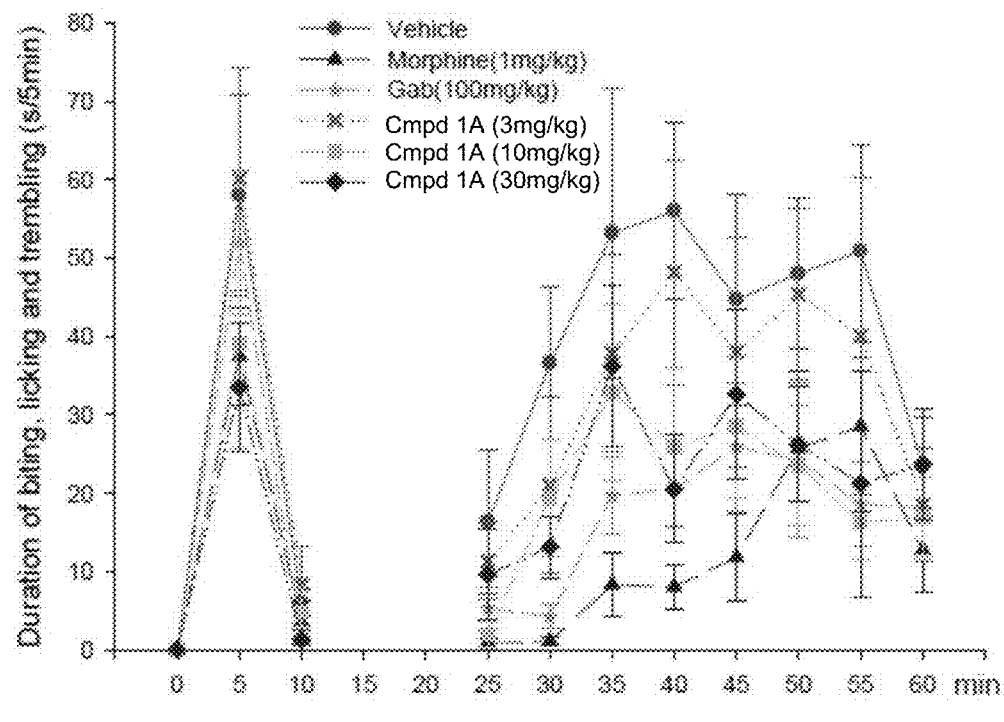
FIG. 3A shows the duration of licking, biting and trembling response as a result of formalin induced pain in rats treated with Compound 1A or indicated reagents during the 60 minutes after formalin injection.
Figure 3B:
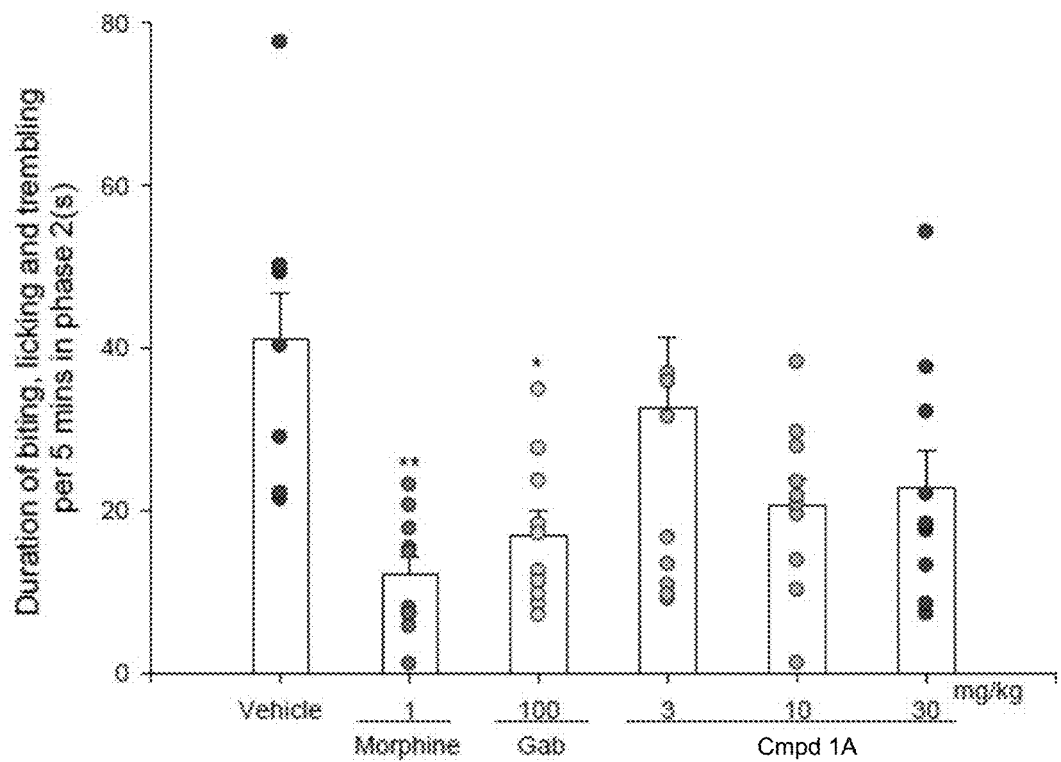
FIG. 3B shows the duration of licking, biting and trembling response as a result of formalin induced pain in rats treated with Compound 1A or indicated reagents in the second phase of pain after formalin injection.

Group mean of average duration of licking, biting and trembling per 5 min is shown in Table 5. Effects of Compound 1A on duration of licking, biting and trembling in the formalin model are shown in FIGS. 3A and 3B.

TABLE 5

Group Mean of Average Duration of Licking, Biting and Trembling (No. per 5 min)

| Group No. | Phase 1 | Phase 2 |
|---|---|---|
| 1 (vehicle) | 32.0 ± 20.3 | 41.1 ± 17.9 |
| 2 (morphine 1 mg/ml) | 20.5 ± 13.1 | 12.1 ± 7.2** |
| 3 (Gab 100 mg/ml) | 26.9 ± 14.7 | 17.1 ± 9.1** |
| 4 (Compound 1A 3 mg/ml) | 34.2 ± 26.8 | 32.6 ± 27.6 |
| 5 (Compound 1A 10 mg/ml) | 21.9 ± 25.1 | 20.7 ± 10.5** |
| 6 (Compound 1A 30 mg/ml) | 17.4 ± 13.0 | 22.9 ± 14.5* |

*$p < 0.05$,
**$p < 0.01$, compared with vehicle group

In summary, Morphine at 1 mg/kg and Gabapentin at 100 mg/kg significantly decreased the duration of licking, biting and trembling post-formalin injection during the period of phase 2. Compound 1A at 10 and 30 mg/kg also had significant effect in comparison with vehicle treated animals during the phase 2 observation period. However, neither the control compounds (morphine and gabapentin) nor Compound 1A (at 3 mg/kg) had any effects during the period of phase 1.

Duration of Total Behaviors (Lifting, Licking, Biting and Trembling)

Figure 4A:
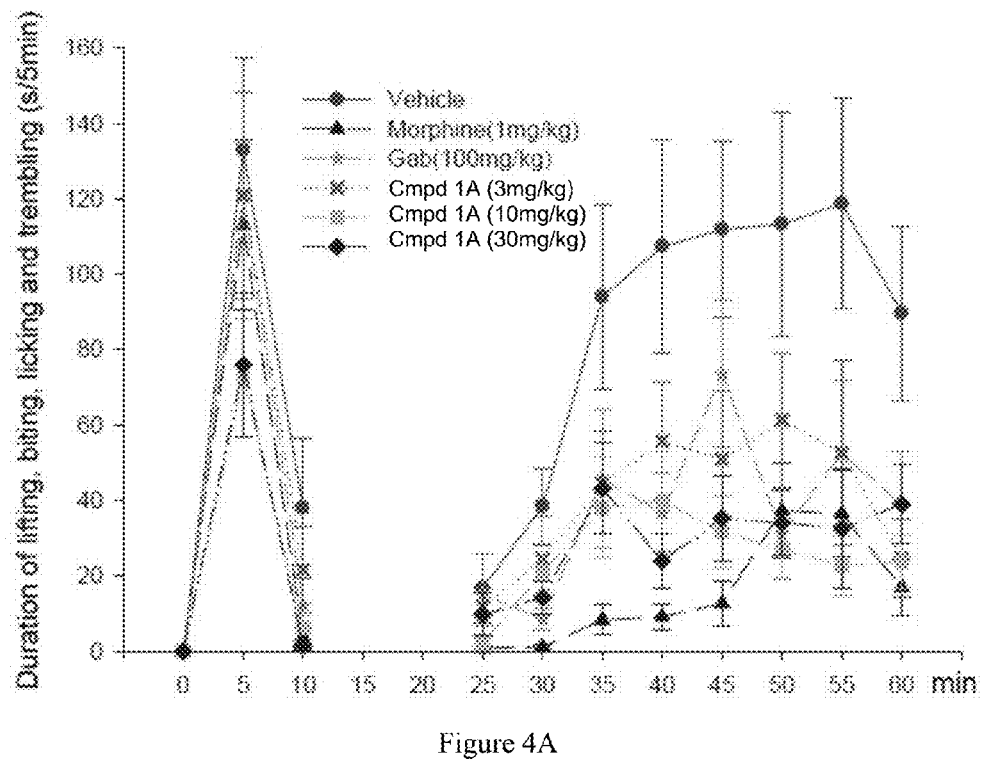
FIG. 4A shows the duration of total behaviors (lifting, licking, biting and trembling) as a result of formalin induced pain in rats treated with Compound 1A or indicated reagents during the 60 minutes after formalin injection.
Figure 4B:
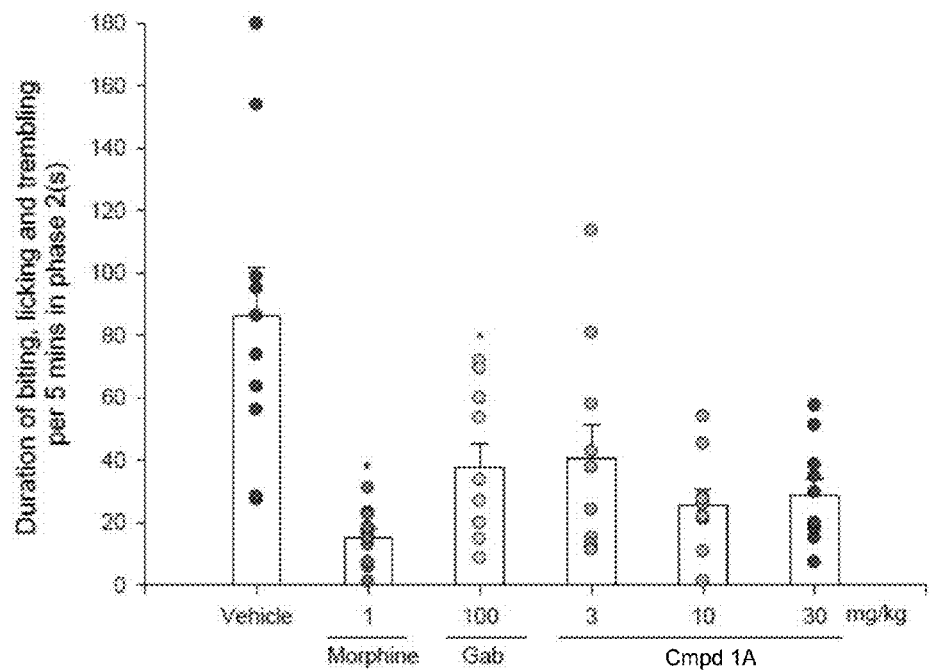
FIG. 4B shows the duration of total behaviors (lifting, licking, biting and trembling) as a result of formalin induced pain in rats treated with Compound 1A or indicated reagents in the second phase of pain after formalin injection.

Group mean of average value of all testing behaviors is shown in Table 6. Effects of Compound 1A on duration of total behaviors in the formalin model are shown in FIGS. 4A and 4B.

Again, all test compounds including Morphine, Gabapentin and Compound 1A at all tested dose levels significantly reduced all testing behaviors post-formalin injection during the period of phase 2. Nonetheless, they had no any effects during the phase 1 observation period.

TABLE 6

Group Mean of Total Testing Behavior (No. per 5 min)

| Group No. | Phase 1 | Phase 2 |
|---|---|---|
| 1 (vehicle) | 85.4 ± 61.6 | 86.2 ± 49.4 |
| 2 (morphine 1 mg/ml) | 58.3 ± 37.7 | 15.3 ± 9.0** |
| 3 (Gab 100 mg/ml) | 66.6 ± 34.8 | 37.8 ± 23.7** |
| 4 (Compound 1A 3 mg/ml) | 71.3 ± 56.4 | 40.8 ± 34.3** |
| 5 (Compound 1A 10 mg/ml) | 39.2 ± 27.5 | 25.8 ± 15.1** |
| 6 (Compound 1A 30 mg/ml) | 38.7 ± 31.8 | 29.0 ± 16.4** |

*$p < 0.05$,
**$p < 0.01$, compared with vehicle group

Overall, Compound 1A had anti-nociceptive effects during the phase 2 observation period post formalin-induced pains, especially at dose level of mid and high (10 mg/kg and 30 mg/kg). However, the dose dependent effect between those two doses seemed inseparable. Between low and mid doses (3 mg/kg and 10 mg/kg), the dose dependent of Compound 1A on anti-nociceptive was more noticeable. Respectively, the control compounds, morphine and Gabapentin, showed consistent effect of inhibiting nociceptive pain as reported on formalin induced pain model.

The invention claimed is:

1. A compound of formula I:

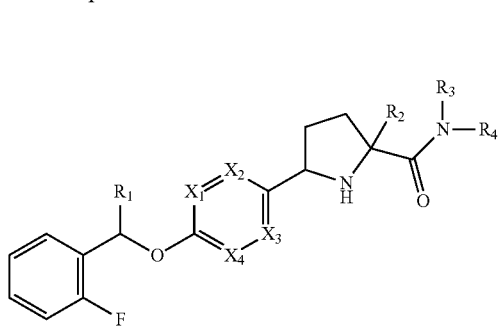

or a pharmaceutically acceptable salt, hydrate, or alcoholate thereof, wherein:

$X_1$, $X_2$, $X_3$, and $X_4$ are each independently selected from N and CH;

$R_1$ is selected from F, $CF_3$, $CH_2F$, $CHF_2$, $OCF_3$, $OCH_2F$, and $OCHF_2$;

$R_2$ is hydrogen; and $R_3$ and $R_4$ are each independently selected from hydrogen and $C_1$-$C_3$ alkyl;

or $R_2$ and $R_3$ or $R_4$ taken together with the atoms to which they are attached form a 5-membered ring.

2. The compound of claim 1, wherein the compound is of formula II:

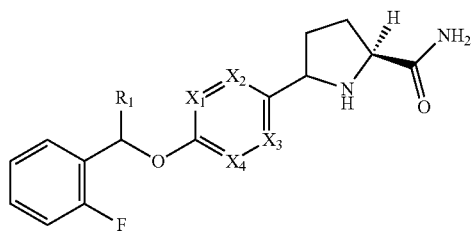

or a pharmaceutically acceptable salt, hydrate, or alcoholate thereof.

3. The compound of claim 1, wherein the compound is of formula III:

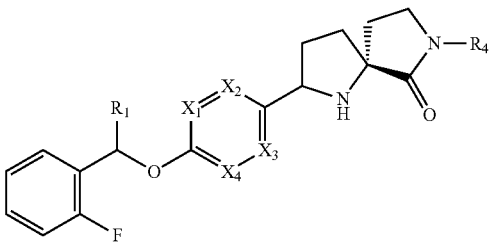

or a pharmaceutically acceptable salt, hydrate, or alcoholate thereof.

4. The compound of claim 1, wherein the compound is of formula IV:

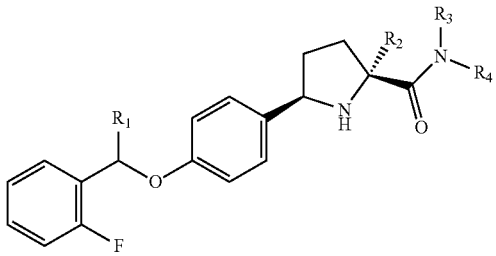

or a pharmaceutically acceptable salt, hydrate, or alcoholate thereof.

5. The compound of claim 1, wherein the compound is of formula V, VI, VII, VIII, or IX:

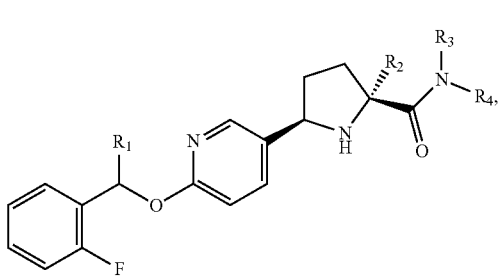

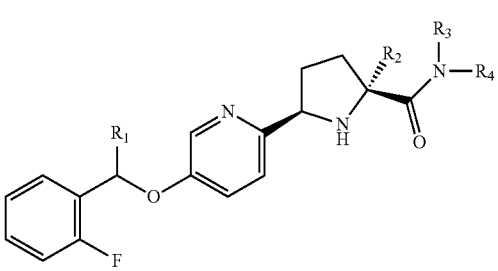

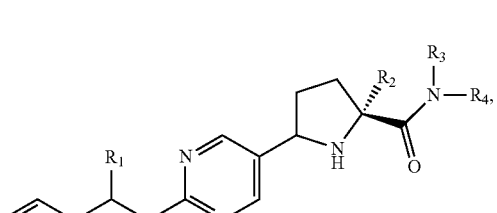

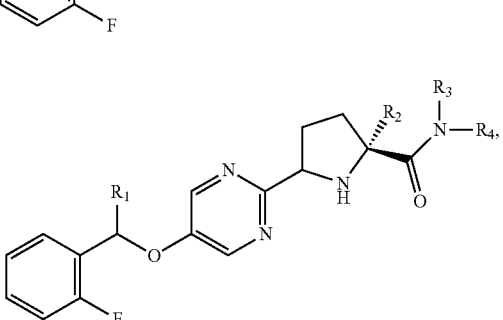

-continued

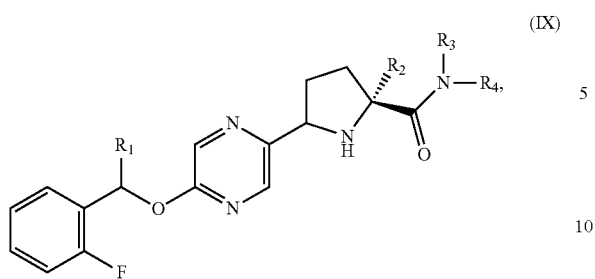
(IX)

or a pharmaceutically acceptable salt, hydrate, or alcoholate thereof.

6. The compound of claim 1, wherein $R_2$ and $R_3$ or $R_4$ taken together with the atoms to which they are attached form a 5-membered ring.

7. The compound of claim 1, wherein $R_3$ or $R_4$ is hydrogen.

8. The compound of claim 1, wherein $R_2$, $R_3$, and $R_4$ are each hydrogen.

9. The compound of claim 1, wherein $R_1$ is selected from F, $CF_3$, $CH_2F$, and $CHF_2$.

10. The compound of claim 9, wherein $R_1$ is $CF_3$.

11. The compound of claim 1, wherein $R_1$ is selected from $OCF_3$, $OCH_2F$, and $OCHF_2$.

12. The compound of claim 11, wherein $R_1$ is $OCF_3$.

13. The compound of claim 1, wherein $R_4$ is $C_1$-$C_3$ alkyl.

14. The compound of claim 1, wherein $R_4$ is methyl, ethyl, or propyl.

15. A compound selected from

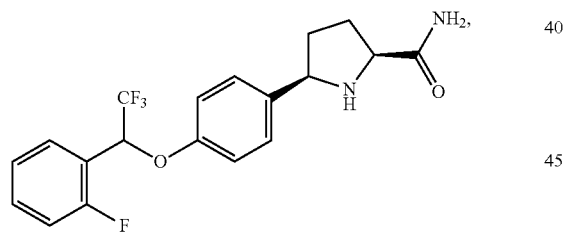

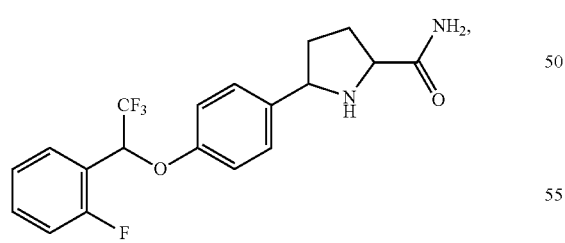

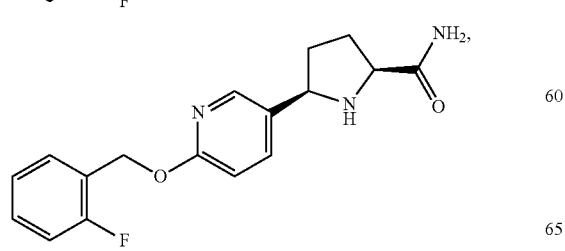

-continued

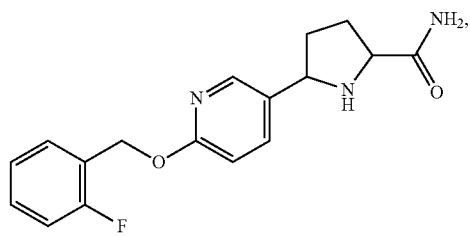

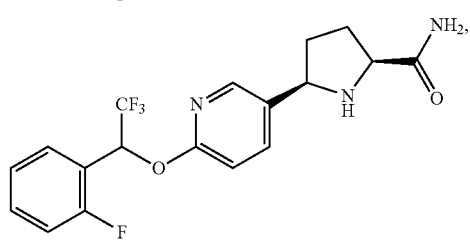 [SMILES: NC(=O)[C@@H]1CC[C@H](c2ccc(OC(c3ccccc3F)C(F)(F)F)nc2)N1]

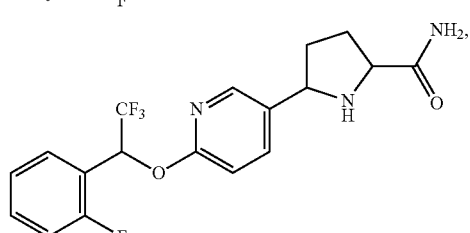

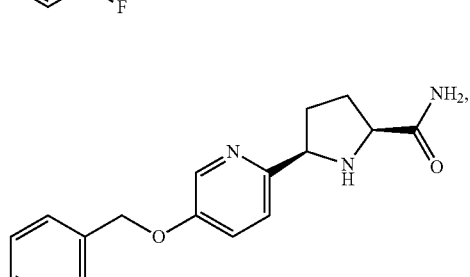

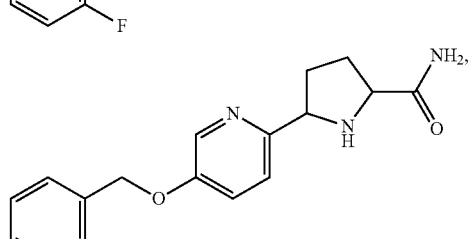

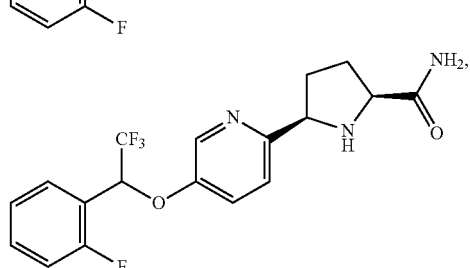

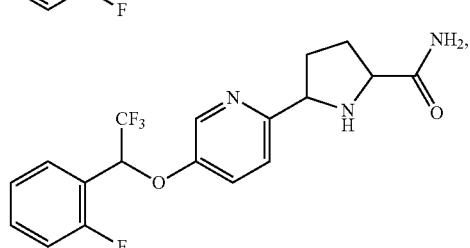

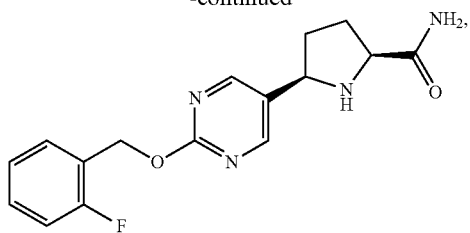
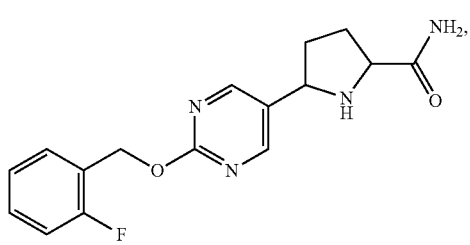 [SMILES: NC(=O)C1CCC(c2cnc(OCc3ccccc3F)nc2)N1]
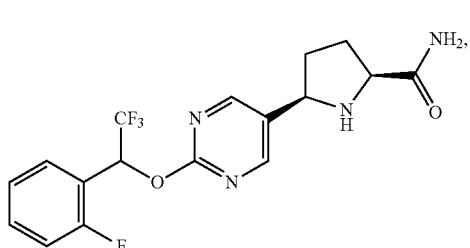
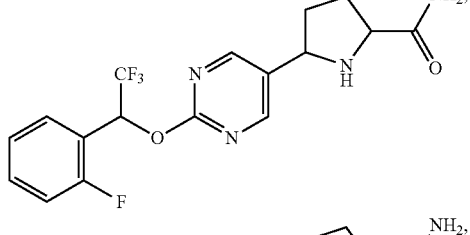
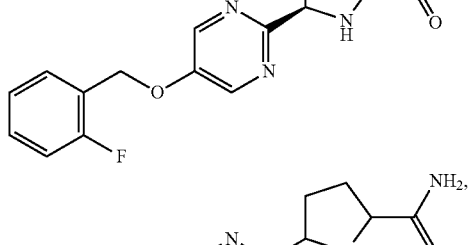
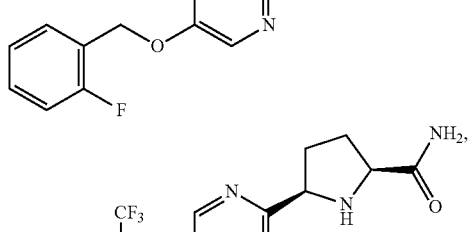
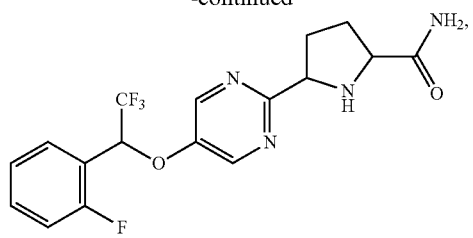
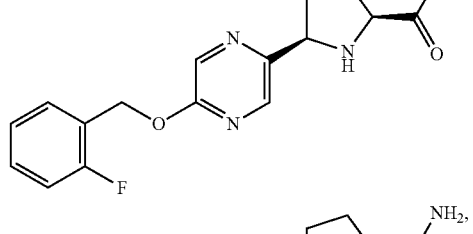
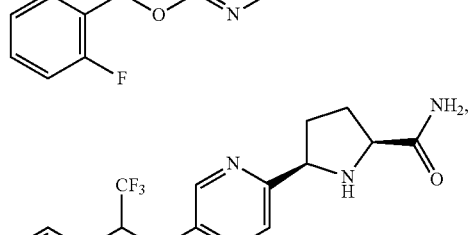
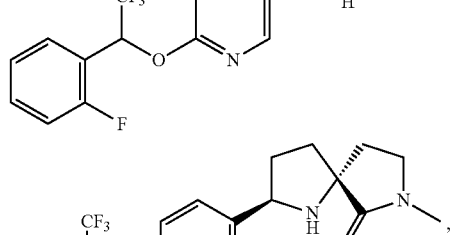
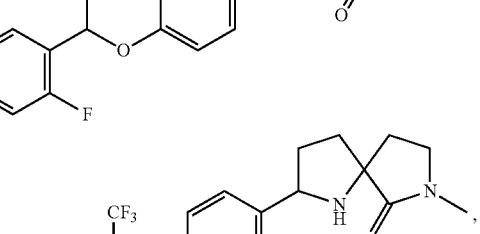
or a pharmaceutically acceptable salt, hydrate, or alcoholate thereof.

16. A pharmaceutical composition comprising a compound of claim 1 or a pharmaceutically acceptable salt, hydrate, or alcoholate thereof and a pharmaceutical carrier, diluent, or excipient.

17. A method of treating a disease or condition selected from epilepsy, inflammatory pain, neuropathic pain, and a bipolar disorder in a subject in need thereof, comprising administering to the subject an effective amount of a compound of claim 1 or a pharmaceutically acceptable salt, hydrate, or alcoholate thereof.

18. A pharmaceutical composition comprising a compound of claim 15 or a pharmaceutically acceptable salt, hydrate, or alcoholate thereof and a pharmaceutical carrier, diluent, or excipient.

19. A method of treating a disease or condition selected from epilepsy, inflammatory pain, neuropathic pain, and a bipolar disorder in a subject in need thereof, comprising administering to the subject an effective amount of a compound of claim 15 or a pharmaceutically acceptable salt, hydrate, or alcoholate thereof.

* * * * *

UNITED STATES PATENT AND TRADEMARK OFFICE
CERTIFICATE OF CORRECTION

PATENT NO. : 9,624,169 B2
APPLICATION NO. : 15/081222
DATED : April 18, 2017
INVENTOR(S) : Ben C. Askew et al.

It is certified that error appears in the above-identified patent and that said Letters Patent is hereby corrected as shown below:

In the Claims

In Claim 15, remove the following compound, shown at Column 52, Line numbers 31-39.

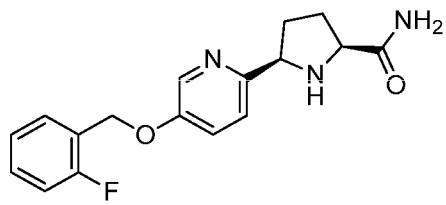

In Claim 15, remove the following compound, shown at Column 52, Line numbers 40-48.

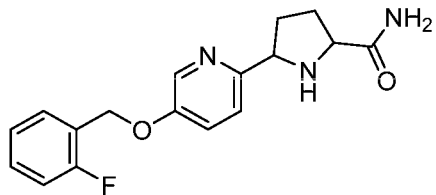

Signed and Sealed this
Fourth Day of July, 2017

Joseph Matal
*Performing the Functions and Duties of the
Under Secretary of Commerce for Intellectual Property and
Director of the United States Patent and Trademark Office*